(12) United States Patent
Ng et al.

(10) Patent No.: US 9,867,574 B2
(45) Date of Patent: Jan. 16, 2018

(54) MULTI-CHANNEL NEURAL SIGNAL AMPLIFIER SYSTEM PROVIDING HIGH CMRR ACROSS AN EXTENDED FREQUENCY RANGE

(71) Applicant: National University of Singapore, Singapore (SG)

(72) Inventors: Kian Ann Ng, Singapore (SG); Yong Ping Xu, Singapore (SG); Shih-Cheng Yen, Singapore (SG); Nitish V. Thakor, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 15/049,235

(22) Filed: Feb. 22, 2016

(65) Prior Publication Data
US 2017/0238876 A1    Aug. 24, 2017

(51) Int. Cl.
| H03F 3/45 | (2006.01) |
| A61B 5/00 | (2006.01) |
| H03F 1/26 | (2006.01) |
| A61B 5/0476 | (2006.01) |
| A61B 5/04 | (2006.01) |

(52) U.S. Cl.
CPC ........ *A61B 5/7203* (2013.01); *A61B 5/04004* (2013.01); *A61B 5/04012* (2013.01);
(Continued)

(58) Field of Classification Search
CPC ................................ H03F 3/45; H03F 1/0288
(Continued)

(56) References Cited

U.S. PATENT DOCUMENTS

| 7,071,780 B2 * | 7/2006 | Van Zanten | ............ H03F 1/086 330/258 |
| 7,200,223 B2 * | 4/2007 | Fortier | ..................... H04B 3/30 324/625 |

(Continued)

OTHER PUBLICATIONS

K. A. Ng et al., "An inductively powered CMOS multichannel bionic neural link for peripheral nerve function restoration," 2012 IEEE Asian Solid State Circuits Conference (A-SSCC), Kobe, 2012, pp. 181-184.

(Continued)

*Primary Examiner* — Henry Choe
(74) *Attorney, Agent, or Firm* — Ming Chow; Sinorica, LLC

(57) ABSTRACT

A high CMRR neural signal amplifier is configured for supply rail common mode feedback (SR-CMFB) whereby a set of CMFB signals is provided to supply rails of front end LNAs. High CMRR is maintained through buffering outputs of front end signal LNAs and a reference LNA coupled to signal and reference inputs of second stage amplifiers, respectively; and buffering the reference LNA output using an active/guard buffer pair, whereby across a plurality of distinct multiplexing time intervals, during each multiplexing time interval one buffer of the pair functions as an active buffer that drives second stage amplifier reference inputs corresponding to second stage amplifier outputs being multiplexed to a set of multiplexor outputs, and the other buffer of the pair functions as a guard buffer coupled to other second stage amplifier reference inputs corresponding to second stage amplifier outputs not being multiplexed to the set of multiplexor outputs.

20 Claims, 27 Drawing Sheets

(52) U.S. Cl.
CPC .............. *A61B 5/0476* (2013.01); *H03F 1/26* (2013.01); *H03F 3/45686* (2013.01); *H03F 2200/261* (2013.01); *H03F 2200/294* (2013.01); *H03F 2203/45288* (2013.01)

(58) Field of Classification Search
USPC ...................................... 330/258, 295, 124 R
See application file for complete search history.

(56) References Cited

U.S. PATENT DOCUMENTS

| | | | | |
|---|---|---|---|---|
| 7,834,696 | B2* | 11/2010 | Giotta | ................. H03F 3/45179 330/258 |
| 2002/0163384 | A1* | 11/2002 | Hasegawa | ........... H03F 3/45071 330/258 |

OTHER PUBLICATIONS

A Bionic Neural Link for peripheral nerve repair. Yong Ping Xu, Shih-Cheng Yen, Kian Ann Ng, Xu Liu, Ter Chyan Tan Conf Proc IEEE Eng Med Biol Soc. 2012; 2012: 1335-1338.

Thomas Jochum, Timothy Denison and PatrickWolf.Integrated circuit amplifiers for multi-electrode intracortical recording. J. Neural Eng. 6 (2009) 012001. pp. 1-26.

C. M. Lopez et al., "An Implantable 455-Active-Electrode 52-Channel CMOS Neural Probe," in IEEE Journal of Solid-State Circuits, vol. 49, No. 1, pp. 248-261, Jan. 2014.

S. Mitra, J. Xu, A. Matsumoto, K. A. A. Makinwa, C. Van Hoof and R. F. Yazicioglu, "A 700μW 8-channel EEG/contact-impedance acquisition system for dry-electrodes," 2012 Symposium on VLSI Circuits (VLSIC), Honolulu, HI, 2012, pp. 68-69.

Obeid I, Morizio JC, Moxon KA, Nicolelis MA, Wolf PD.Two multichannel integrated circuits for neural recording and signal processing.IEEE Trans Biomed Eng. Feb. 2003;50(2):255-8.

Obeid I, Nicolelis MA, Wolf PD.A low power multichannel analog front end for portable neural signal recordings.J Neurosci Methods. Feb. 15, 2004;133(1-2):27-32.

R. G. Carvajal et al., "The flipped voltage follower: a useful cell for low-voltage low-power circuit design," in IEEE Transactions on Circuits and Systems I: Regular Papers, vol. 52, No. 7, pp. 1276-1291, Jul. 2005.

H. Ott, Noise Reduction Techniques in Electronic Systems, 2nd Edition. Wiley-Interscience, 1988.

* cited by examiner

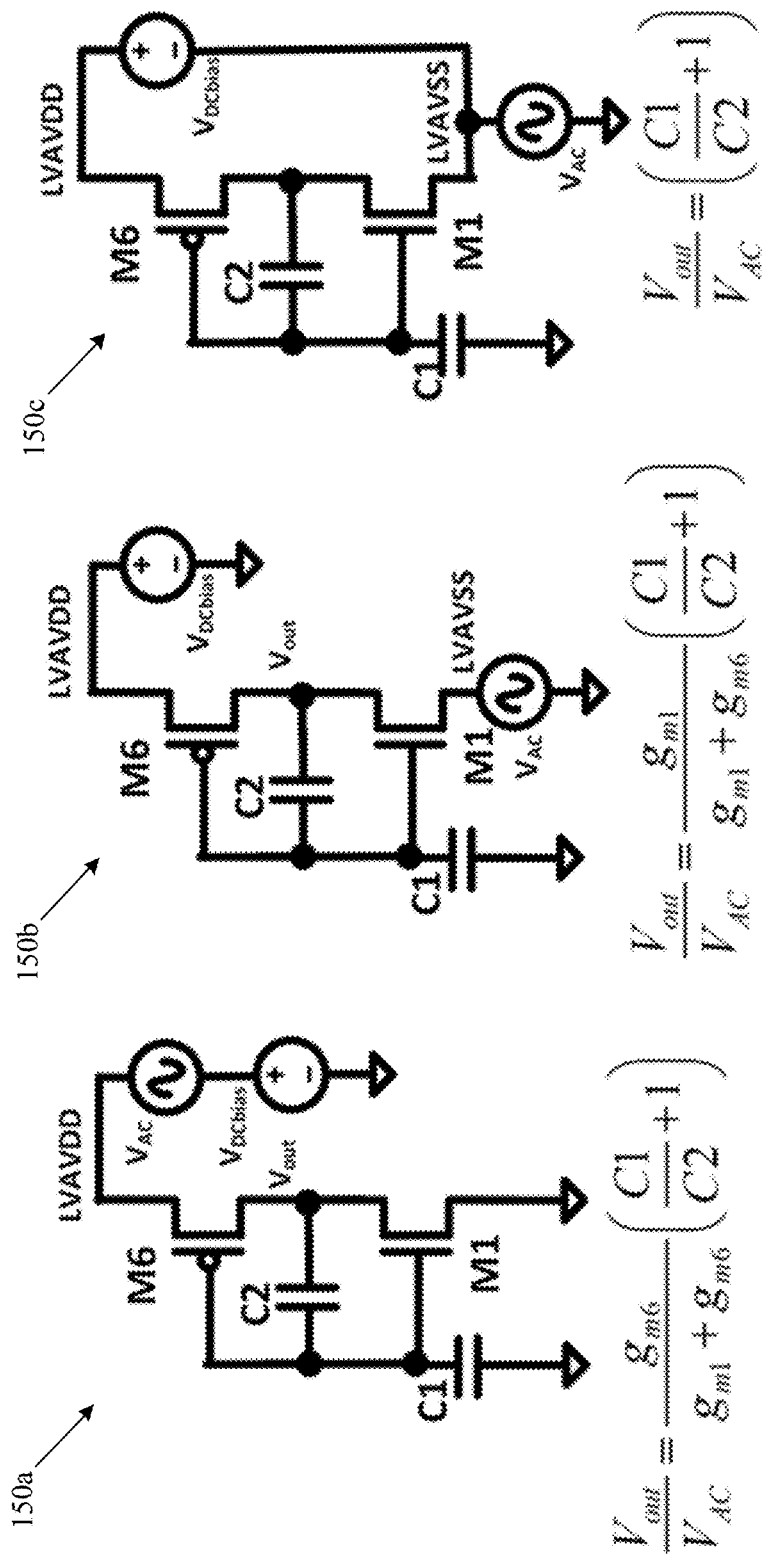

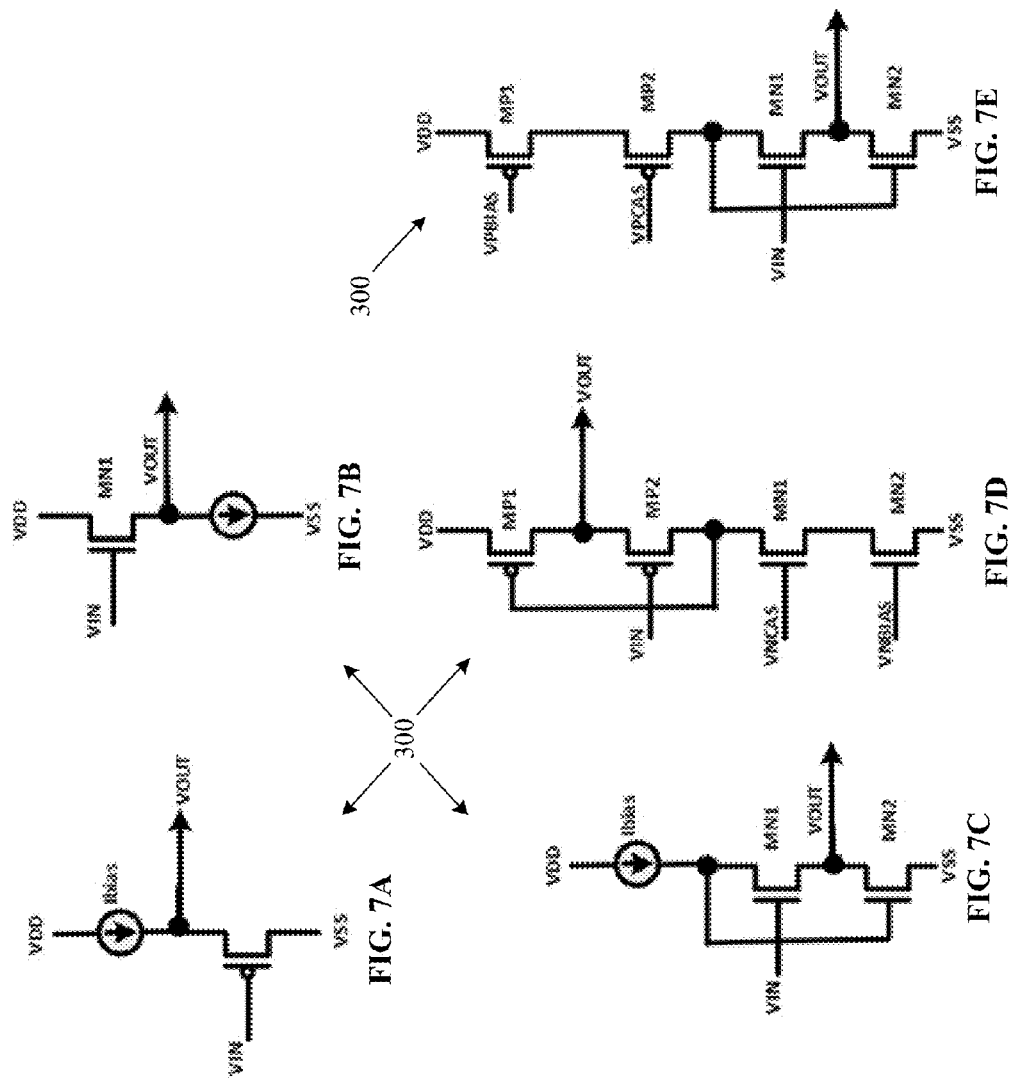

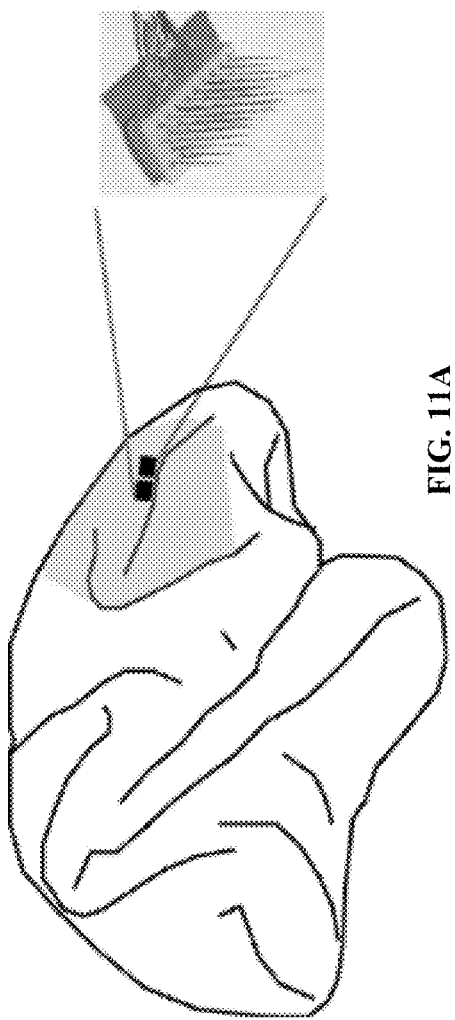
FIG. 11A
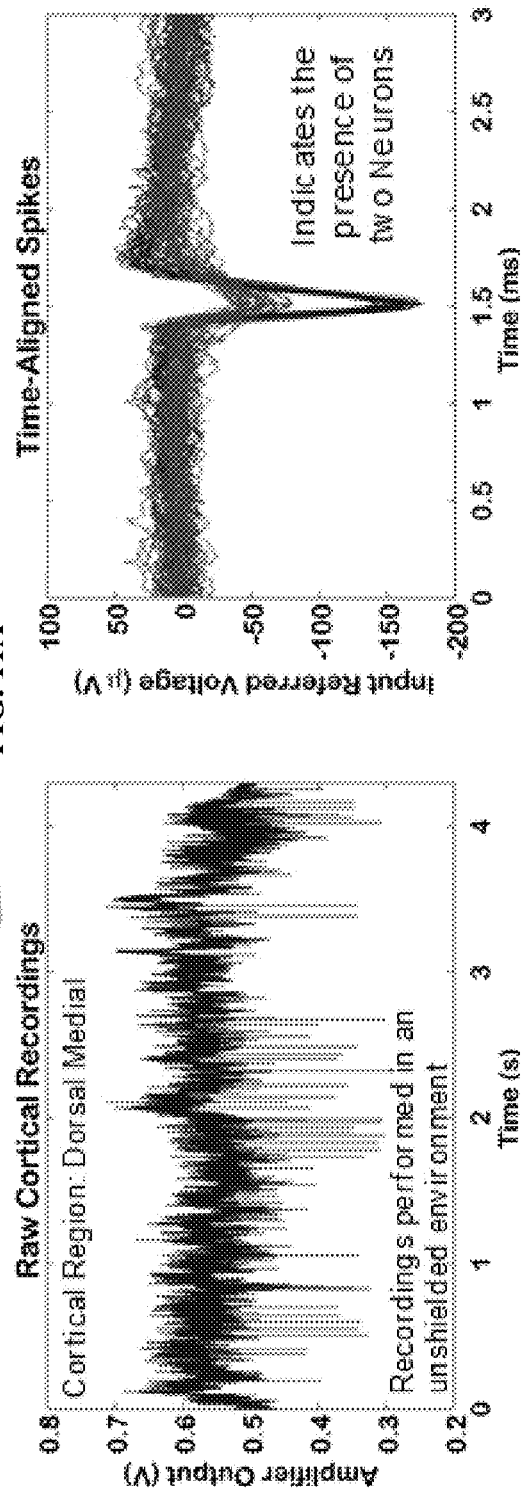
FIG. 11C
FIG. 11B

MULTI-CHANNEL NEURAL SIGNAL AMPLIFIER SYSTEM PROVIDING HIGH CMRR ACROSS AN EXTENDED FREQUENCY RANGE

TECHNICAL FIELD

Aspects of the present disclosure relate generally to biopotential amplifiers, and more particularly, neural signal amplifiers. Still more particularly, aspects of the present disclosure are directed to a multi-channel neural signal amplifier system that exhibits a high common mode rejection ratio (CMRR) across a wide or extended frequency range.

BACKGROUND

Biopotential amplifiers are essential building blocks in multiple types of biological signal sensing or recording systems. For instance, neural signal amplifiers or neural amplifiers are essential building blocks of neural signal sensing or recording systems. Ideally, a neural signal amplifier should exhibit high input impedance, low power consumption, low Noise Efficiency Factor (NEF) concurrent with low Power Efficiency Factor (PEF), and minimal sensitivity to input referred noise. Furthermore, a neural signal amplifier should be able to significantly reject common-mode interference (CMI). Sources of strong CMI include AC mains 50/60 Hz interference, and possibly muscle electromyographic (EMG) artifacts.

FIG. 1A is a schematic illustration showing portions of an embodiment of a representative conventional multi-channel neural signal amplifier 1, which includes a front end, front end circuitry, or an input stage 10; and a second stage or second stage circuitry 40. The front end 10 includes a low noise amplifier (LNA) corresponding to each neural signal recording channel. Each of such LNAs has an input that is coupled to a neural signal recording electrode by which the recording channel LNA can receive an input neural signal, and hence each of such LNAs can be referred to as a signal LNA. The front end 10 also includes a reference LNA corresponding to a reference channel, where the reference LNA includes an input to which a reference signal can be provided by way of a reference electrode. The second stage 40 includes a second stage amplifier G2 corresponding to each channel, which has a signal input (e.g., its non-inverting input as per FIG. 1A) coupled to an output of a counterpart front end signal LNA, and which has a reference input (e.g., its inverting input as per FIG. 1A) coupled to the output of the reference LNA. Thus, for a neural signal amplifier having N channels, the output of the reference LNA is replicated across the reference inputs of N second stage amplifiers G2. As a result, the representative neural signal amplifier 1 of FIG. 1A can be referred to as having a replica reference topology.

For any given channel 1 ... N (e.g., N=16 in a representative implementation), the second stage amplifier G2 performs a differential signal subtraction between the input neural signal for that channel and the reference signal, and provides a corresponding channel output voltage $V_{out\ 1\ \ldots\ N}$. As will be readily understood by individuals having ordinary skill in the relevant art, prior to the differential signal subtraction by each second stage amplifier G2, each signal LNA amplifies both input neural signals and CMI signals. If the CMI signals are large, the signal LNAs can easily become saturated, thereby disrupting any ongoing neural signal amplification, for instance, in a manner indicated in FIG. 1B, which shows representative neural input signals, saturated signals output by the signal LNAs, and saturated signals output by the second stage amplifiers G2. This saturation problem can be particularly significant for modern neural signal amplifiers that operate at low supply voltages, and which require front end LNAs having high gain. For a representative conventional neural signal amplifier 1 having front end LNAs designed to accommodate input signals having a maximum input peak-to-peak amplitude of 12 mV to produce a maximum output voltage of 250 mV peak-to-peak, as shown in FIG. 1C, in the presence of CMI signals having an amplitude of up to 100 mV peak-to-peak, the front end LNAs can easily saturate.

A common mode feedback (CMFB) technique can be employed to reduce the gain of the front end LNAs and hence enhance the input common mode swing. More specifically, as illustrated in FIG. 1D, a CMFB signal generator 50 having a summing amplifier can be added to the conventional neural signal amplifier 1 of FIG. 1A to produce a modified neural signal amplifier 5 that provides a CMFB signal to a non-inverting terminal of each front end LNA, while input neural signals are provided to an inverting terminal of each signal LNA and the reference signal is provided to an inverting terminal of the reference LNA. FIG. 1D also illustrates representative signal flow through the modified neural signal amplifier 5 in the presence of input CMI signals. As a result of the CMFB, the front end LNAs attenuate CMI signals, common mode gain is reduced, and intrinsic CMRR (ICMRR) is increased. FIG. 1E illustrates representative signal flow through the modified neural signal amplifier 5 when a neural signal having a nonzero amplitude is applied to the input of one of the signal LNAs, while the other signal LNAs receive zero amplitude signals at their inputs. FIG. 1F illustrates representative signal flow through the modified neural signal amplifier 5 in the presence of input referred noise, showing that the CMFB signal generator 50 does not contribute to input referred noise.

In spite of its advantages, this common mode feedback technique requires that each front end LNA of the modified neural signal amplifier 5 be a differential amplifier, which unfortunately requires an extra input terminal for each front end LNA, and which undesirably results in additional power consumption and larger circuit area.

In addition to the foregoing, in the representative conventional neural signal amplifier 1 of FIG. 1A as well as the modified neural signal amplifier 5 of FIG. 1D, the reference LNA drives the reference inputs across all second stage amplifiers G2, while each signal LNA drives the input capacitance of only its corresponding second stage amplifier G2. The output of the reference LNA thus encounters a different load capacitance than the output of each signal LNA.

FIG. 1G illustrates this load capacitance mismatch situation for the conventional neural signal amplifier 1 of FIG. 1A, showing that for N channels, the reference LNA drives a load capacitance that is N times higher than the load capacitance driven by any given signal LNA. More particularly, for N input channels, the total effective input capacitance seen at the reference LNA input is given by $$C_{LNA\_REF} = \frac{N \cdot C_1 \cdot (C_{fb})}{C_1 + C_{fb}} \approx N \cdot (C_{fb}) \text{ for } C_1 >> C_{fb} \qquad (1)$$

When all front end LNAs are driven by a CMI signal, the effective input capacitance seen at each signal LNA input is derived to be $$C_{LNA\_SIG} = \frac{C_1 \cdot (C_{fb})}{C_1 + C_{fb}} \approx C_{fb}, \text{ for } C_1 >> C_{fb} \quad (2)$$

and thus for N>=2, the output of the reference LNA encounters a larger load capacitance than that encountered by the output of each signal LNA.

Further to the foregoing, the front end LNAs are usually designed using operational transconductance amplifiers (OTAs) that intrinsically have high output impedance, as they have to be biased with low biasing current to keep the total power consumption low. This high output impedance in conjunction with the load capacitance presented by the input capacitances of the second stage amplifier G2 forms a pole which determines the high side 3-dB cutoff frequency, $f_u$. For higher N, the reference LNA's $f_u$ is markedly lower than that of the signal LNAs. This means the phase response of the reference LNA and the signal LNAs are markedly different. When a common mode signal appears at all front end LNA inputs, the signals output by the front end LNAs and appearing at the two inputs of the second stage amplifier G2 have non-zero phase difference for frequencies above DC, for instance, in a manner representatively illustrated in FIG. 1H.

The second stage amplifier G2 amplifies this phase difference and essentially performs a differential phase-to-amplitude conversion, which is a form of common mode-to-differential signal conversion that increases with increasing signal frequency, for instance, in a manner shown in FIG. 1I. Thus, the phase difference arising from the difference in capacitive loading at the output of the reference LNA versus that at the output of each signal LNA undesirably increases common mode gain, which degrades the intrinsic common mode rejection ratio (ICMRR) as input signal frequency increases (i.e., this phase difference causes ICMRR to decrease with increasing signal frequency).

A need exists for a neural signal amplifier system that overcomes the foregoing problems.

SUMMARY

In accordance with an aspect of the present disclosure, a biopotential amplifier includes an input stage having a plurality of inputs and a plurality of outputs, the input stage including: (a) a plurality of signal low noise amplifiers (LNAs) including a signal LNA corresponding to each channel, each signal LNA for a given channel having an input configured for receiving a biopotential signal corresponding to the given channel, an output, a supply terminal (LNAVDD terminal) corresponding to a positive supply rail at which a supply signal is providable, and a ground terminal (LNAVSS terminal) corresponding to a negative supply rail couplable to electrical ground; and a reference low noise amplifier (LNA) having an input configured for receiving a reference signal, an output, a supply terminal (LNAVDD terminal) corresponding to a positive supply rail at which a supply signal is providable, and a ground terminal (LNAVSS terminal) corresponding to a negative supply rail couplable to electrical ground; (b) a second stage including a second stage amplification and/or processing unit, which for a given channel has each of a signal input coupled to the output of the signal LNA and an output corresponding to the given channel, the second stage amplification and/or processing unit further including at least one reference input coupled to the output of reference LNA; and (c) a common mode feedback (CMFB) signal generator configured to provide a set of CMFB signals to at least one supply rail of the input stage.

The CMFB signal generator can include for any given channel a signal input coupled to the output of the signal LNA for the given channel; a reference input coupled to the output of the reference LNA; and at least one of (a) a first output coupled to the LNAVDD terminal of the reference LNA and the LNAVDD terminal of each signal LNA, and (b) a second output coupled to the LNAVSS terminal of the reference LNA and the LNAVSS terminal of each signal LNA. For instance, the CMFB signal generator can include each of: (a) a first output coupled to the LNAVDD terminal of each signal LNA and the LNAVDD terminal of the reference LNA, by which a first CMFB signal produced by the CMFB signal generator is providable to each signal LNA and the reference LNA; and (b) a second output coupled to the LNAVSS terminal of each signal LNA and the LNAVSS terminal of the reference LNA, by which a second CMFB signal produced by the CMFB signal generator is providable to each signal LNA and the reference LNA.

The reference LNA and each signal LNA can be single-ended amplifiers. For instance, the reference LNA and each signal LNA can include or be a capacitively coupled inverter-based LNA (CCI_LNA). A CCI_LNA can include or be a CMOS inverter-based operational transconductance amplifier (CI_OTA), wherein the CI_OTA provides the LNAVDD terminal and the LNAVSS terminal of the CCI_LNA.

In accordance with an aspect of the present disclosure, the biopotential amplifier can include plurality of buffers, including for each channel a first buffer coupled between the output of the signal LNA and the signal input of the second stage amplification and/or processing unit corresponding to that channel. Each buffer within the plurality of buffers can be a unity gain buffer or a non-unity gain buffer, for instance, a flipped voltage follower (FVF).

In accordance with an aspect of the present disclosure, the biopotential amplifier can include: a plurality of multiplexors having a plurality of inputs coupled to the outputs of the second stage amplification and/or processing unit and a set of multiplexor outputs, the plurality of multiplexors configured to sequentially multiplex distinct subsets of second stage amplification and/or processing unit outputs to the set of multiplexor outputs across a plurality of distinct multiplexing time intervals; and a pair of active/guard buffers within which during any given multiplexing time interval one buffer of the active/guard buffer pair operates as an active buffer and the other buffer of the active/guard buffer pair operates as a guard buffer, each of the active buffer and the guard buffer having an input coupled to the output of the reference LNA and an output, wherein during any given multiplexing time interval the output of the active buffer is coupled to a distinct subset of second stage amplification and/or processing unit outputs being multiplexed to the set of multiplexor outputs during the given multiplexing time interval, while the output of the guard buffer is coupled to other second stage amplification and/or processing unit outputs not being multiplexed to the set of multiplexor outputs during the given multiplexing time interval. Each of the active buffer and the guard buffer comprises a unity gain buffer or a non-unity gain buffer, for instance, an FVF.

Across a plurality of distinct multiplexing time intervals, each buffer of the pair of active/guard buffers alternatingly operates as the active buffer or the guard buffer from one multiplexing time interval to another multiplexing time interval. The plurality of multiplexor outputs can be coupled to an output pad driver and/or other downstream circuitry that is coupled to a set of output pads, such that during any given multiplexing time interval the distinct subset of second stage amplification and/or processing unit outputs coupled to the output of the active buffer during the given multiplexing time interval is coupled to the set of output pads.

In accordance with an embodiment of the present disclosure, a process is provided for detecting, sensing, or recording, or amplifying biopotentials using a biopotential amplifier having (a) an input stage comprising a plurality of inputs and a plurality of outputs, (b) a second stage comprising a plurality of signal inputs, a reference input, and a plurality of outputs, and (c) a common mode feedback (CMFB) signal generator comprising a plurality of inputs coupled to the plurality of input stage outputs and a set of outputs. The process includes: receiving a plurality of biopotential signals at a corresponding plurality of inputs of signal low noise amplifiers (LNAs) of the input stage, each signal LNA including an input, an output, a supply terminal (LNAVDD terminal), and a ground terminal (LNAVSS terminal); receiving a reference signal at a reference input of a reference LNA of the input stage, the reference LNA including an input, an output, a supply terminal (LNAVDD terminal), and a ground terminal (LNAVSS terminal); coupling signals output by the signal LNAs to corresponding signal inputs of second stage amplification and/or processing unit of the second stage; coupling a reference signal output by the reference LNA to at least one reference input of the second stage amplification and/or processing unit; coupling signals output by each signal LNA and the reference signal output by the reference LNA to the inputs of the CMFB signal generator; generating a set of CMFB signals with the CMFB generator corresponding to the signals provided to the CMFB signal generator inputs; and providing supply rail based CMFB (SR-CMFB) to the input stage by feeding back the set of CMFB signals to at least one of the LNAVDD terminal and the LNAVSS terminal of each signal LNA and the reference LNA.

Each signal LNA and the reference LNA can be a single-ended capacitively coupled LNA (CCLNA) having an operational transconductance amplifier (OTA) therein, wherein the OTA corresponding to each signal LNA and the reference LNA provides the LNAVDD terminal and the LNAVSS terminal thereof. The OTA can comprise an inverter.

The set of CMFB signals can includes a first CMFB signal and a second CMFB signal, and providing SR-CMFB to the input stage includes feeding back the first CMFB signal to the LNAVDD terminal of each signal LNA and the LNAVDD terminal of the reference LNA, and feeding back the second CMFB signal to the LNAVSS terminal of each signal LNA and the LNAVSS terminal of the reference LNA.

The process can further include receiving the output of each signal LNA at a buffer corresponding to the signal LNA, and coupling an output of this buffer to a corresponding signal input of the second stage amplification and processing unit.

In accordance with some embodiments of the process, the biopotential amplifier can further include (d) an output stage including a plurality of multiplexors having a plurality of inputs coupled to the second stage amplification and/or processing unit outputs and a set of outputs, the plurality of multiplexors configured to sequentially multiplex distinct subsets of second stage signal amplification and/or processing unit outputs to the set of multiplexor outputs across a plurality of distinct multiplexing time intervals, and (e) an active/guard buffer pair having a first buffer and a second buffer, each of the first buffer and the second buffer of the active/guard buffer pair having an input coupled to the output of the reference LNA and each of the first buffer and the second buffer of the active/guard buffer pair having an output. In such embodiments, the process can further include: receiving the output of the reference LNA at the inputs of the first and second buffers of the active/guard buffer pair; and across a plurality of distinct multiplexing time intervals, alternatingly operating each of the first buffer and the second buffer of the active/guard buffer pair as an active buffer or the guard buffer from one multiplexing time interval to another multiplexing time interval, such that during a given multiplexing time interval, the output of the active buffer is coupled to a distinct subset of second stage amplification and/or processing unit outputs being multiplexed to the set of multiplexor outputs during the given multiplexing time interval, while the output of the guard buffer is coupled to other second stage amplification and/or processing unit outputs not being multiplexed to the set of multiplexor outputs during the given multiplexing time interval.

BRIEF DESCRIPTION OF THE DRAWINGS

FIGS. 3A-3E show representative circuit configurations for establishing a non-inverting input terminal for a front end CI_OTA by way of the CI_OTA's supply terminal (LNAVDD) and/or ground terminal (LNAVSS) in accordance with particular embodiments of the present disclosure.

FIGS. 7A-7E show representative embodiments of unity gain buffers in accordance with alternate embodiments of the present disclosure.

FIGS. 11A-11C show results of an experiment in which the as-fabricated neural signal amplifier of FIG. 9 was used to acquire cortical signals from the dorsal medial region of an awake *Macaca fasciularis*.

DETAILED DESCRIPTION

Figure 1A:
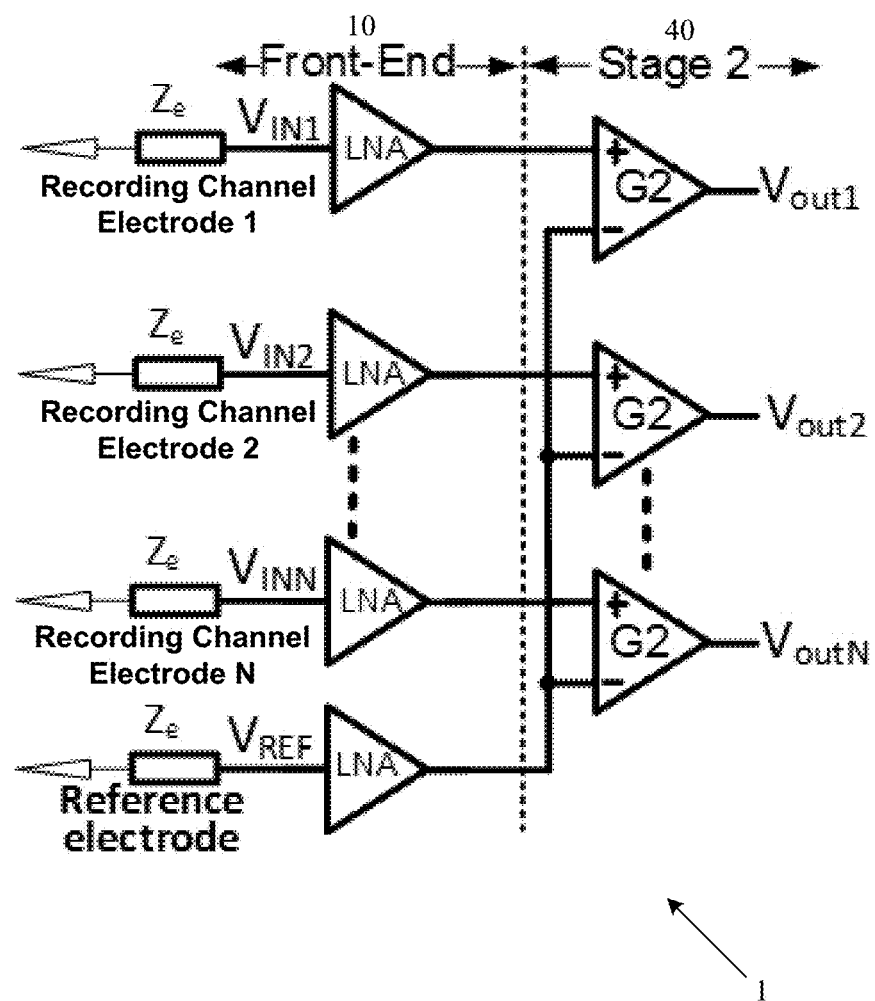
FIG. 1A is a schematic illustration showing portions of a representative conventional multi-channel neural signal amplifier.
Figure 1B:
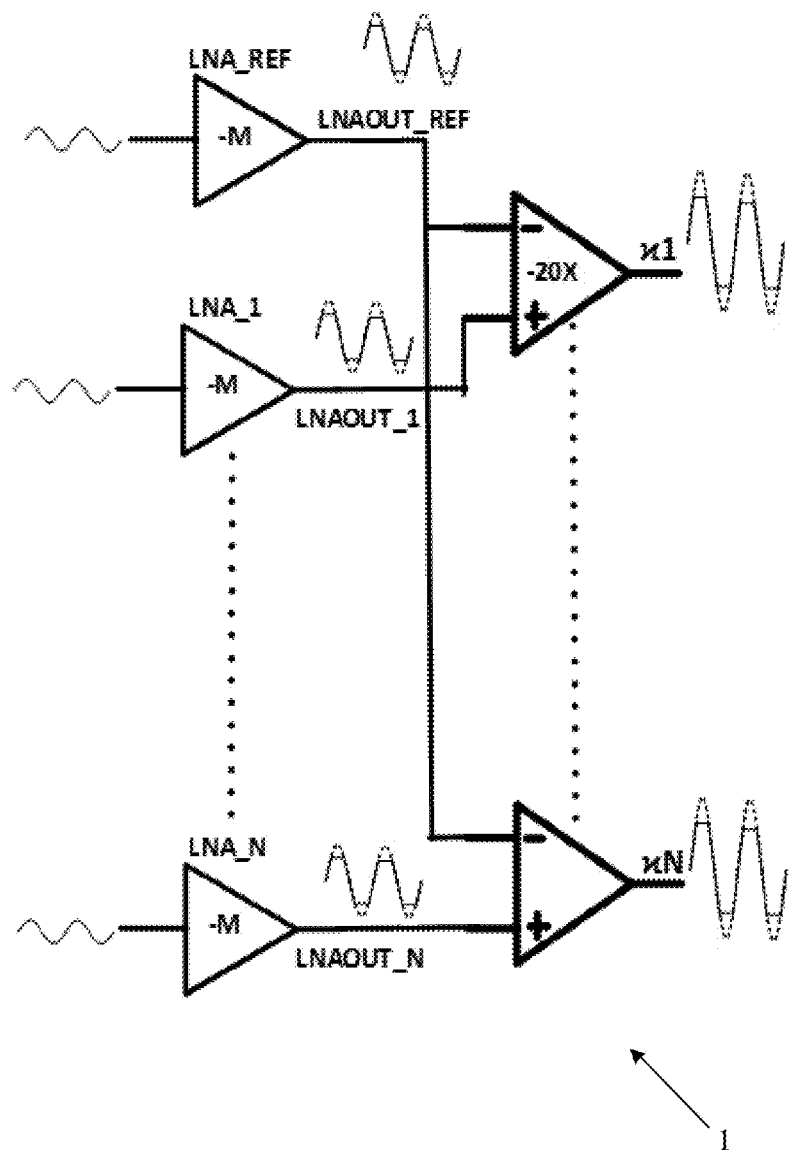
FIG. 1B shows a representative manner in which front end signal Low Noise Amplifiers (LNAs) of the conventional neural signal amplifier of FIG. 1A can become easily saturated as a result of common mode interference (CMI) signals, thereby disrupting ongoing neural signal amplification.
Figure 1C:
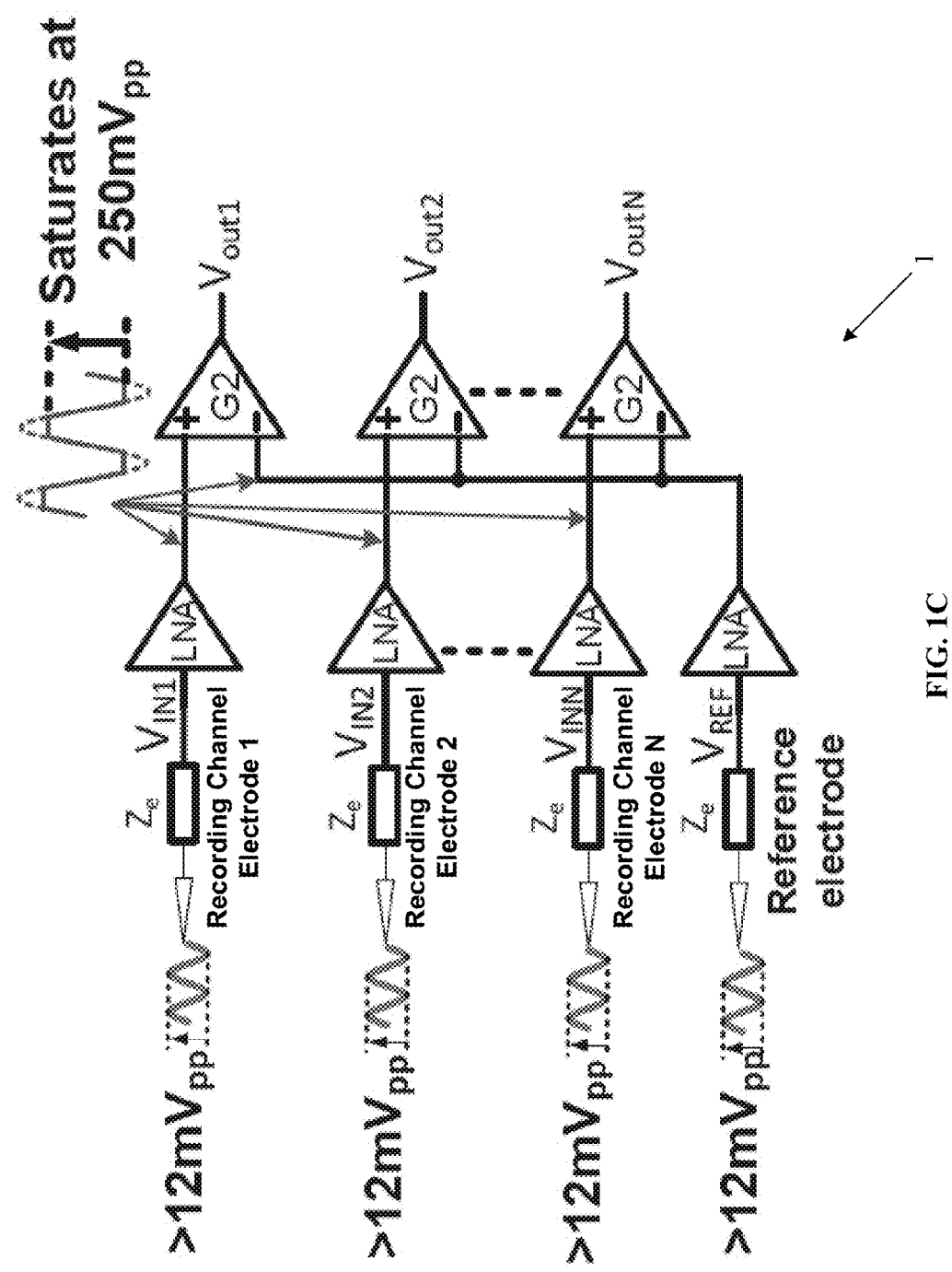
FIG. 1C illustrates front end signal LNA saturation at 250 mV peak-to-peak in the presence of CMI signals having an amplitude of up to 100 mV peak-to-peak for the conventional neural signal amplifier of FIG. 1A having front end LNAs designed to accommodate input signals having a maximum input peak-to-peak amplitude of 12 mV.
Figure 1D:
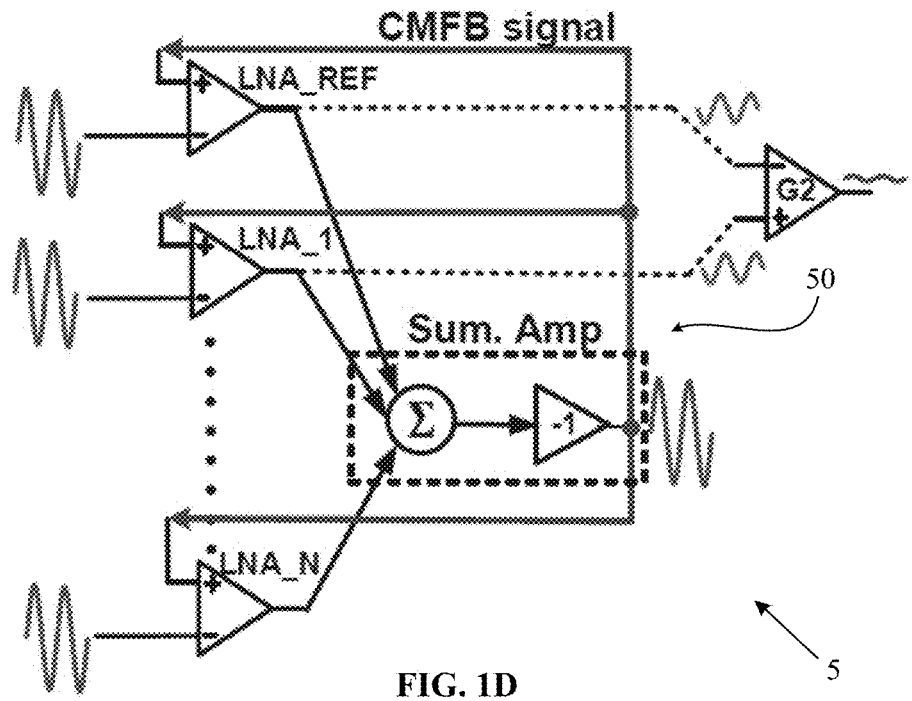
FIG. 1D illustrates a conventional neural signal amplifier of FIG. 1A that has been modified in accordance with a conventional common mode feedback (CMFB) technique to enhance input common mode swing.
Figure 1E:
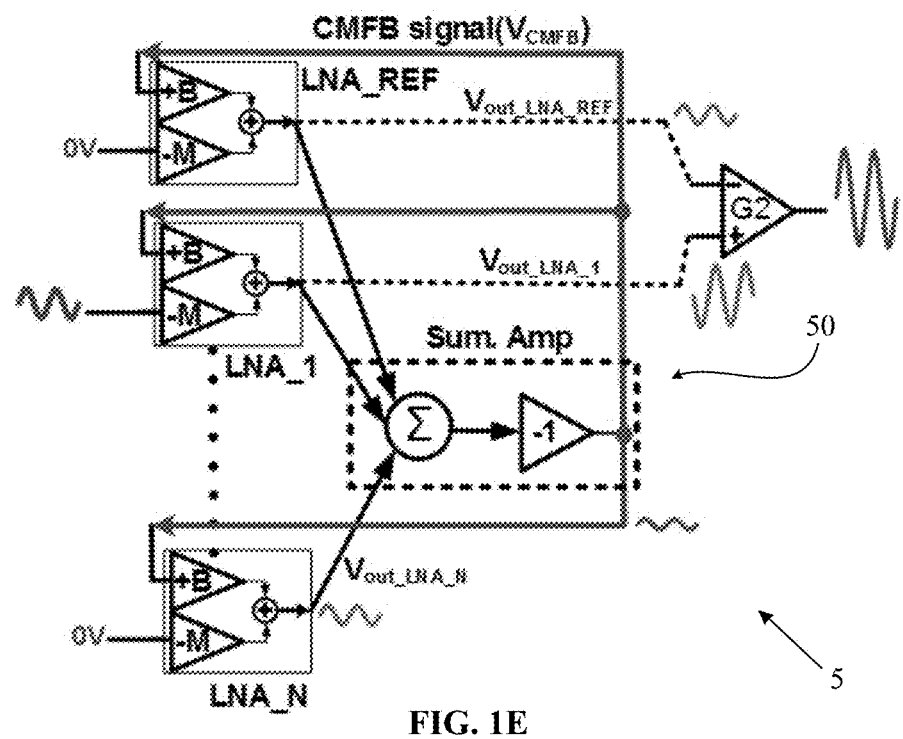
FIG. 1E illustrates representative signal flow through the modified neural signal amplifier of FIG. 1D when a neural signal having a nonzero amplitude is applied to the input of one signal LNA, while other signal LNAs receive zero amplitude signals at their inputs.
Figure 1F:
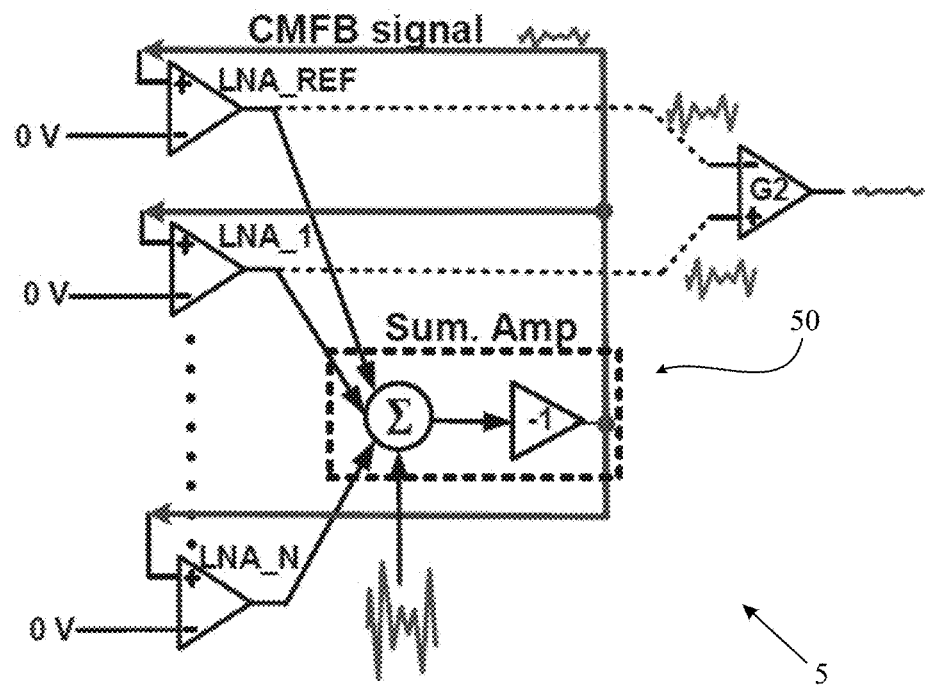
FIG. 1F illustrates representative signal flow through the modified neural signal amplifier of FIG. 1D in the presence of input referred noise.
Figure 1G:
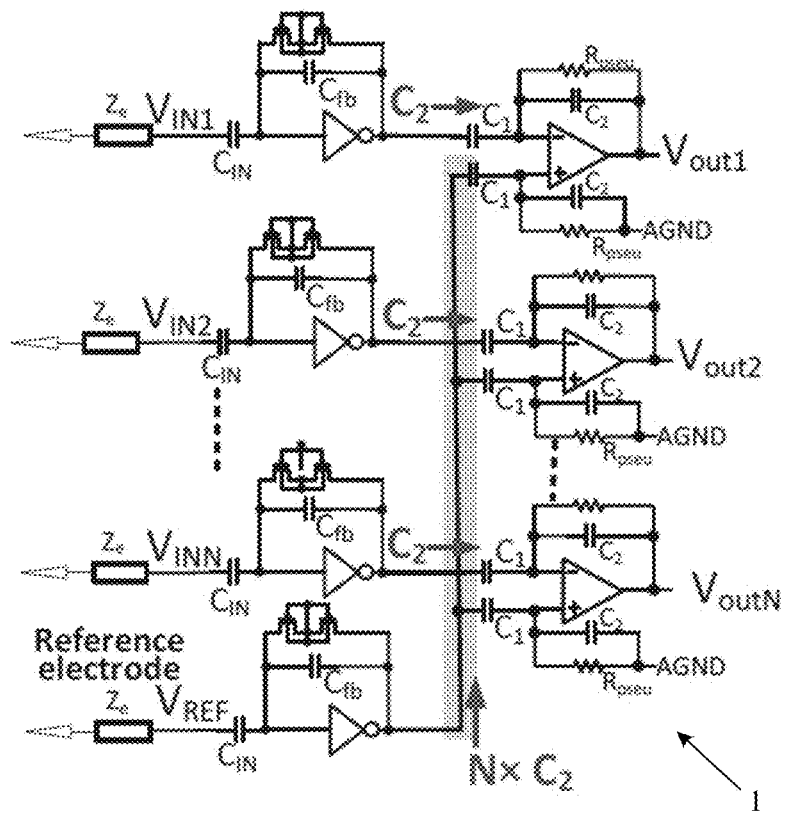
FIG. 1G illustrates a load capacitance mismatch situation for the conventional neural signal amplifier 1 of FIG. 1A.
Figure 1H:
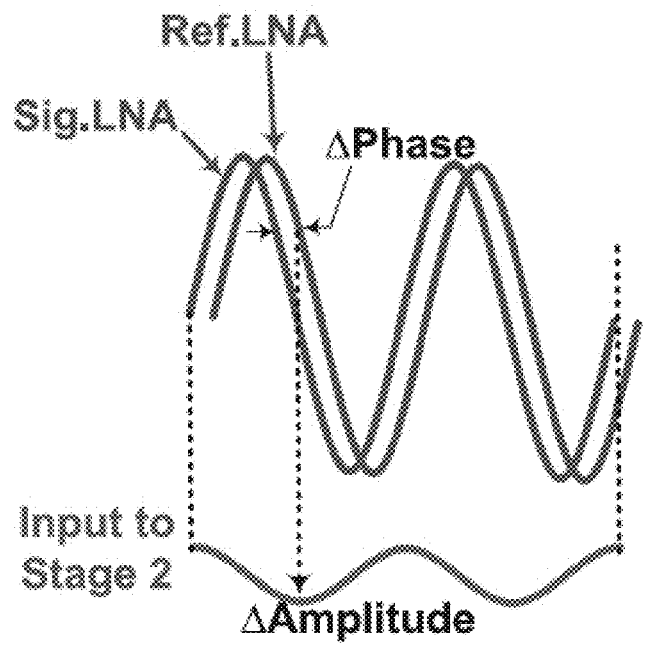
FIG. 1H illustrates a representative non-zero phase difference between signals output by the reference LNA and the signal LNAs of the conventional neural signal amplifier of FIG. 1A as a result of the load capacitance mismatch situation shown in FIG. 1G.
Figure 1I:
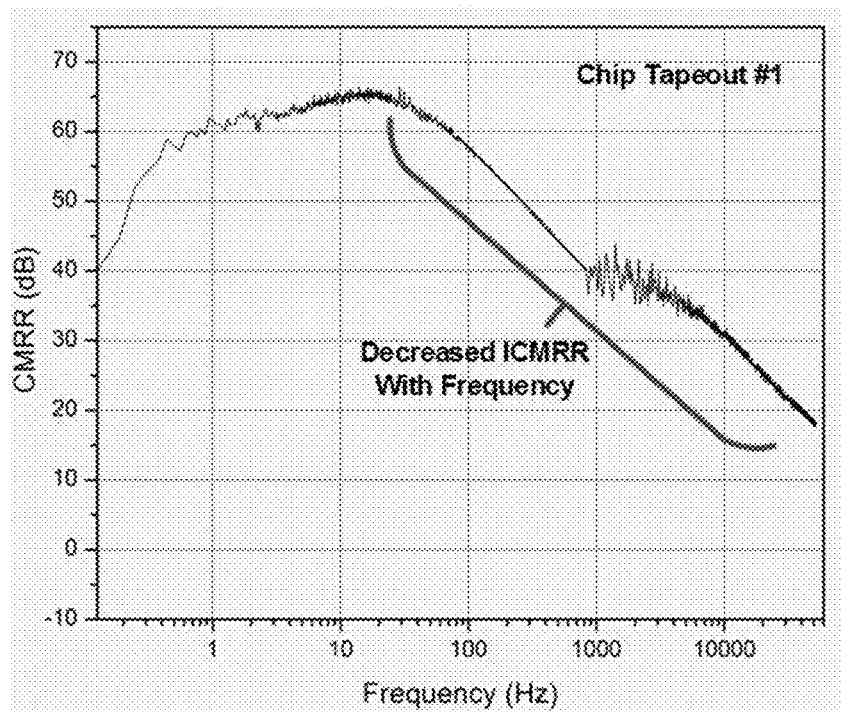
FIG. 1I illustrates a representative manner in which a second stage amplifier performs a common mode-to-differential signal conversion corresponding to the non-zero phase difference shown in FIG. 1H, which increases with increasing signal frequency.

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

Overview

Embodiments in accordance with the present disclosure are directed to a multi-channel or N channel biopotential amplifier system or biopotential amplifier that is well-suited for neural signal recording (e.g., a neural signal amplifier system or neural signal amplifier), which exhibits or provides high CMRR, and which addresses or compensates for phase shift between the reference LNA output and the signal LNA outputs across a wide, enhanced, or extended frequency range to thereby exhibit or maintain high CMRR across the wide, enhanced, or extended frequency range. Embodiments in accordance with the present disclosure include an input stage having a plurality of signal LNAs and a reference LNA; and a subsequent, next, or second stage coupled to the input stage, where the second stage includes a signal amplification and/or processing unit. In some embodiments, the signal amplification and/or processing unit can include a second stage amplifier G2 corresponding to each channel; in other embodiments, the signal amplification and/or processing unit can include or be a digital signal processing unit (e.g., a digital signal processor (DSP), which can be conventional), in manner readily understood by individuals having ordinary skill in the relevant art. Individuals having ordinary skill in the relevant art will also understand that an embodiment in accordance with the present disclosure can include one or more other stages in addition to the input stage and the second stage described herein. For purpose of simplicity and clarity, in representative embodiments described and shown herein, N is 16; however, individuals having ordinary skill in the relevant art will understand that N can be greater than or less than 16, depending upon embodiment details or a biopotential or neural signal amplification situation under consideration.

As further described in detail below, embodiments in accordance with the present disclosure exhibit or provide a high CMRR by way of supply rail common mode feedback (SR-CMFB) through which a set of CMFB signals is provided to the supply rails of single-ended capacitively coupled LNAs (CCLNAs) of a front end or input stage. Embodiments in accordance with the present disclosure can thus avoid the use of differential front end LNAs, resulting in reduced power consumption and smaller circuit area. In various embodiments, each CCLNA is a capacitively coupled inverter based LNA (CCI_LNA) having a CMOS inverter based OTA (CI_OTA) therein, which is power efficient, and which exhibits low NEF and a compact spatial area.

Multiple embodiments in accordance with the present disclosure can suppress the aforementioned phase-to-differential amplitude conversion effect to thereby exhibit or maintain high CMRR across a wide, enhanced, or extended frequency range (e.g., the entire, essentially the entire, or nearly the entire operating bandwidth of the neural signal amplifier) by way of (a) a unity gain or non-unity gain buffer between the output of each signal LNA and a corresponding signal input of a second stage amplification and/or processing unit (e.g., a signal input of a corresponding second stage amplifier G2); and/or (b) a pair of unity gain or non-unity gain buffers, each of which is coupled to the output of the reference LNA. The buffers corresponding to the signal LNAs as well as each buffer of the pair of buffers corresponding to the reference LNA can be implemented as flipped voltage followers (FVFs). For purpose of brevity and clarity and to aid understanding, in various parts of the description herein the buffers corresponding to the signal LNAs as well as each buffer of the pair of buffers corresponding to the reference LNA are representatively described unity gain buffers, though this need not be the case in all embodiments.

With respect to the signal LNAs, the unity gain buffer coupled to the output of each signal LNA has a much lower output impedance compared to the signal LNA to which it is coupled, thereby reducing the output impedance of the signal LNA, which reduces the phase shift issue at low frequencies. With respect to the reference LNA, the pair of unity gain buffers is configured for limiting the number of reference inputs of the second stage signal amplification and/or processing unit (e.g., the number of reference inputs of the second stage amplifiers G2) that the reference LNA needs to drive at any given time or during any given time interval (e.g., a multiplexing time interval). For instance, out of an entire set of second stage amplifiers G2, during any given time interval one of the pair of unity gain buffers acts as an active unity gain buffer that drives the reference inputs of a distinct subset or subgroup of second stage amplifiers G2 having outputs that are actively being multiplexed to a set of pad buffers during the time interval under consideration; while the other of the pair of unity gain buffers acts as a guard unity gain buffer that drives the reference inputs of the remaining second stage amplifiers G2 having outputs that are not actively being multiplexed to the set of pad buffers during the time interval under consideration. Consequently, the reference LNA does not drive the reference inputs of the entire set of second stage amplifiers G2 at any time, but rather sequentially drives the reference inputs of distinct subset or subgroups of second stage amplifiers G2 from one time interval to another. As a result, the load capacitance mismatch between the reference LNA and the signal LNAs is significantly reduced, and the phase shift issue is reduced including at higher frequencies.

Aspects of Representative Neural Signal Amplifier Embodiments

Figure 2A:
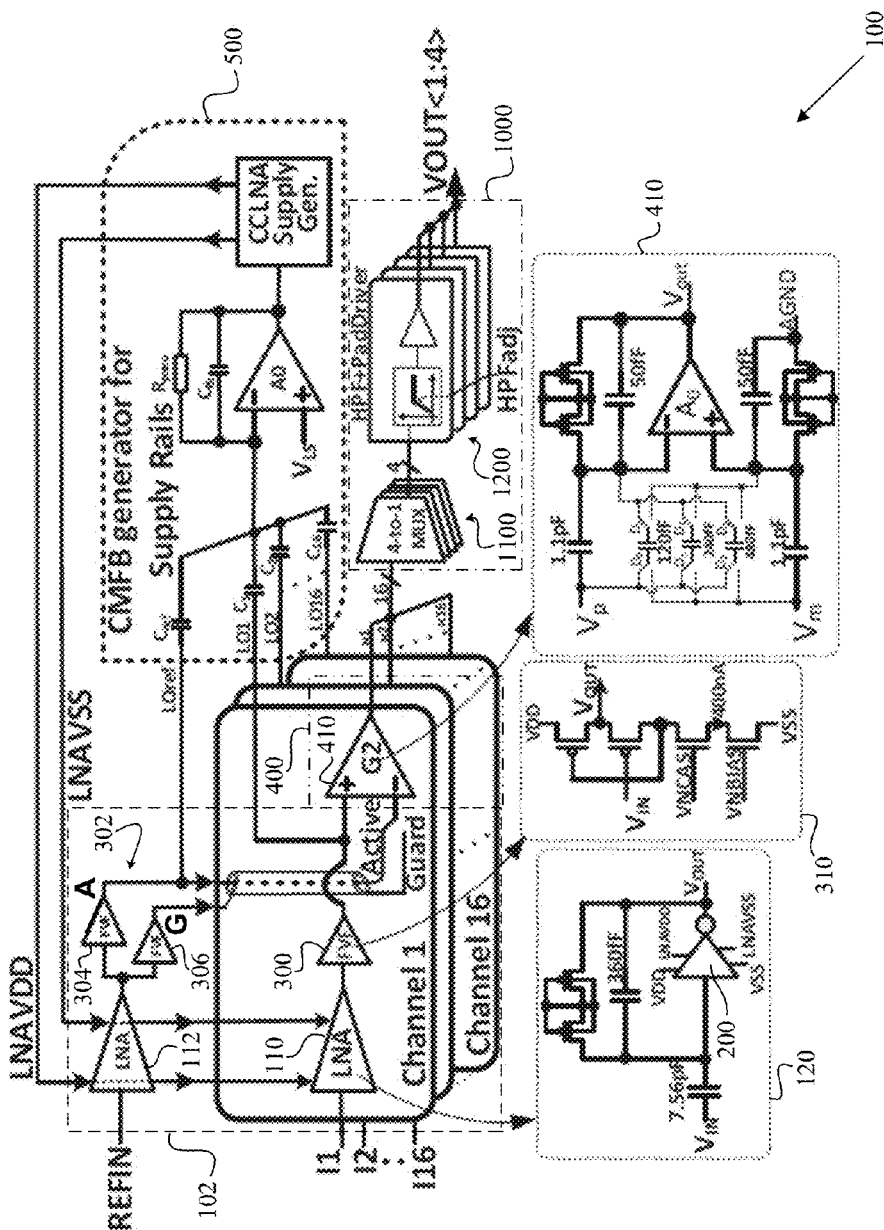
FIG. 2A is a schematic illustration of a multi-channel or N channel biopotential amplifier system or biopotential amplifier suitable for neural signal recording, or a multi-channel neural signal amplifier system or multi-channel neural signal amplifier in accordance with an embodiment of the present disclosure.

FIG. 2A is a schematic illustration of a multi-channel or N channel biopotential amplifier system or biopotential amplifier 100 suitable for neural signal recording, or a multi-channel neural signal amplifier system, multi-channel neural signal amplifier, or multi-channel neural amplifier 100 in accordance with an embodiment of the present disclosure. Individuals having ordinary skill in the relevant art will understand that embodiments in accordance with the present disclosure can be employed in multiple types of bioelectronic/neuroelectronic systems or devices, such as biomodulation/neuromodulation devices and bioprosthesis/neuroprosthesis devices.

In various embodiments, the neural signal amplifier 100 includes a front end or input stage 102 having a single-ended capacitively coupled signal LNA 110 corresponding to each channel, plus a single-ended capacitively coupled reference LNA 112; a second stage 400 providing a second stage amplification and/or processing unit 410; a CMFB signal generator 500 coupled to the input stage 102 and configured to provide SR-CMFB to each signal LNA 110 and the reference LNA 112 by way of using their supply rails as inputs for the CMFB signal; and a next, subsequent, or output stage 1000 that includes a plurality of multiplexors 1100 coupled to an output pad driver 1200 and/or other downstream circuitry (not shown) that provides couplings to a set of output pads (e.g., a plurality of output pads, not shown) in a manner readily understood by individuals having ordinary skill in the relevant art.

Depending upon embodiment details, the second stage signal amplification and/or processing unit 410 can include or be a plurality of amplifiers (e.g., a differential amplifier corresponding to each channel) and/or a DSP. For any given channel, the second stage signal amplification and/or processing unit 410 includes a signal input corresponding to the output of that channel's signal LNA 110, and an output corresponding to that channel. The second stage signal amplification and/or processing unit 410 also includes at least one reference input corresponding to the output of the reference LNA 112, in accordance with embodiment and/or implementation details. For instance, the second stage signal amplification and/or processing unit 410 can include for each channel a reference input corresponding to that channel. For purpose of brevity and clarity and to aid understanding, in the description that follows the second stage amplification and processing unit 410 is representatively described and shown as a plurality of second stage amplifiers 410/G2, though this need not be the case in all embodiments.

Figure 2B:
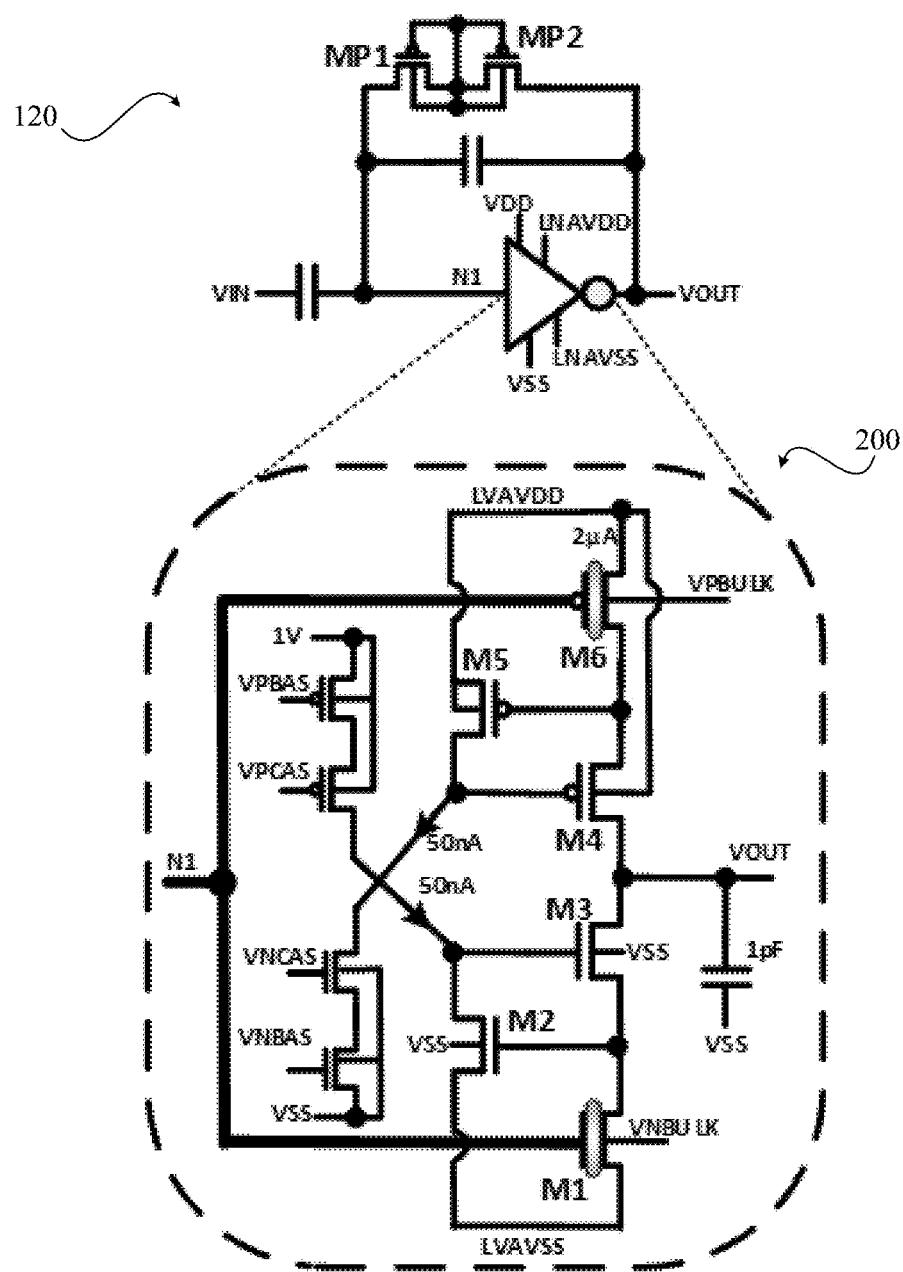
FIG. 2B illustrates a capacitively coupled inverter-based LNA (CCI_LNA) and a circuit diagram of a corresponding CMOS inverter-based output transconductance amplifier (CI_OTA) thereof in accordance with an embodiment of the present disclosure.

With respect to the input stage 102, each signal LNA 110 is a CCI_LNA 120 has an input coupled to receive a biopotential such as a neural signal, and an output coupled to a buffer such as a unity gain buffer 300, which in multiple embodiments is an FVF 310. The CCI_LNA 120 can include a CMOS inverter based OTA (CI_OTA) 200 therein, which is power efficient, and which exhibits low NEF and a compact spatial area. FIG. 2B illustrates a CCI_LNA 120 and a circuit diagram of a corresponding CI_OTA 200 thereof in accordance with an embodiment of the present disclosure.

The reference LNA 112 is also a CCI_LNA 120, which has an input coupled to receive a reference signal, and which has the same gain as each signal LNA 110 in a manner readily understood by individuals having ordinary skill in the relevant art. The reference CCI_LNA 120 can include a CI_OTA 200 therein, in the same manner as for each signal CCI_LNA 110. The reference LNA 112 further has an output coupled to a pair of buffers such as a pair of unity gain buffers 302 within which an active (A) unity gain buffer 304 and a guard (G) unity gain buffer 306 can be defined with respect to sequentially or successively driving distinct subsets or subgroups of the reference inputs of the second stage amplifiers 410/G2 across sequential or successive time intervals (e.g., distinct multiplexing time intervals). More particularly, during a given time interval, the active unity gain buffer 304 corresponding to that time interval drives the reference inputs of a predetermined subset or subgroup of second stage amplifiers 410/G2 having outputs that are being actively multiplexed to the output pad driver 1200, while concurrently, the guard unity gain buffer 306 corresponding to that time interval drives the reference inputs of the other second stage amplifiers 410/G2 that are not being actively multiplexed to the output pad driver 1200. In multiple embodiments, the active unity gain buffer 304 and the guard unity gain buffer 306 are FVFs 310.

With respect to the second stage 400, in several embodiments each second stage amplifier 410/G2 is a differential capacitively coupled amplifier, which can be conventional. Individuals having ordinary skill in the art will recognize that this second stage can also be any amplifier that has a differential inputs that have non-zero input capacitance. In multiple embodiments, each second stage amplifier 410/G2 includes a folded cascode operational amplifier (opamp) $A_O$ as the active amplifier element, which has PMOS differential inputs and a class AB translinear output stage. Such an embodiment can include a capacitor bank, such as a 3 bit capacitor bank, to correct for gain mismatch between each signal CCI_LNAs 120 and the reference CCI_LNA 112 arising from intra-die process variation, in a manner understood by individuals having ordinary skill in the relevant art. Individuals having ordinary skill in the art will also recognize that the second stage amplifier 410/G2 can be implemented as another type of opamp or operational transconductance amplifier, and hence is not limited to a folded cascade opamp. As indicated above, individuals having ordinary skill in the art will recognize that alternate embodiments, a DSP can replace on or more second stage amplifiers 410/G2.

Aspects of Providing SR-CMFB to Single-Ended Front End LNAs

Figure 2C:
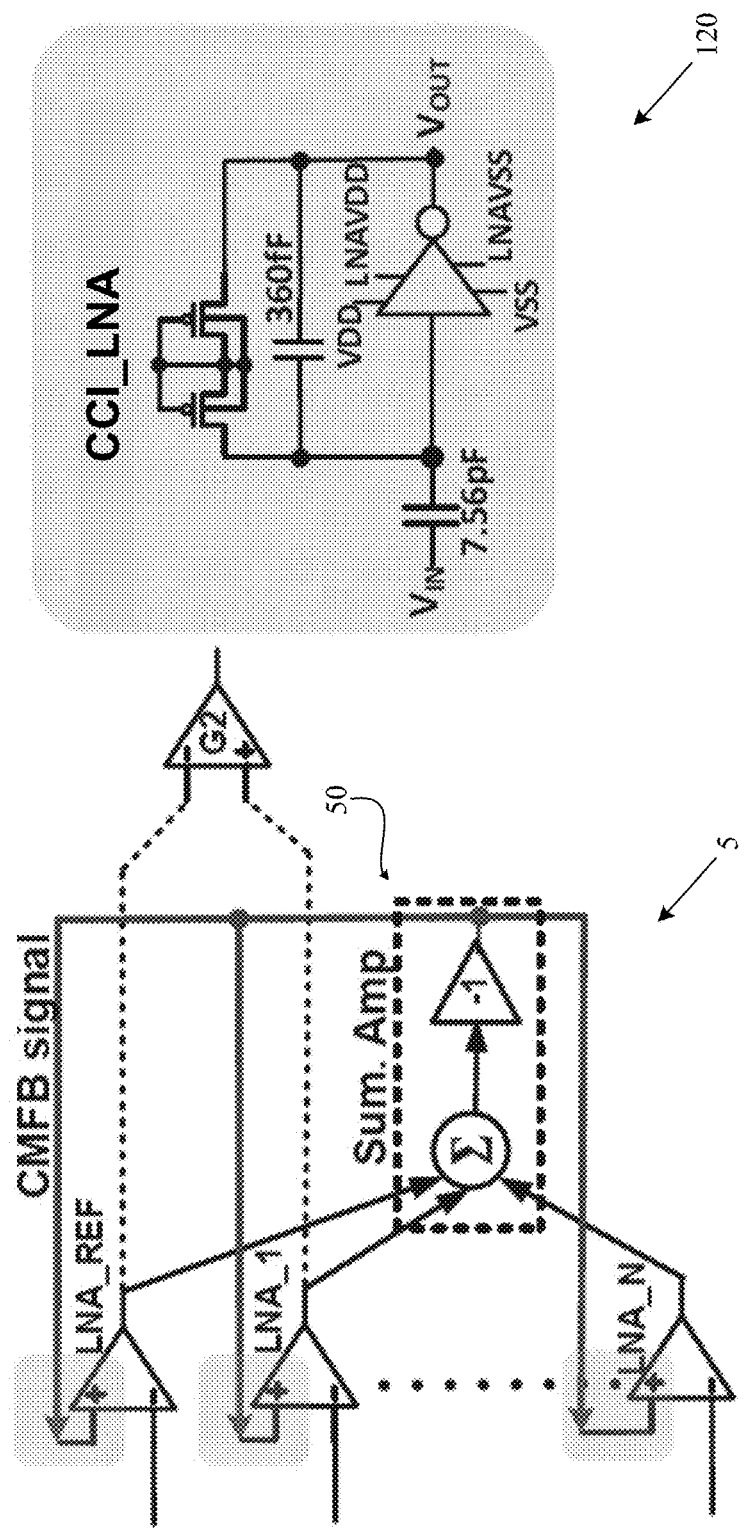
FIG. 2C illustrates a lack of a conventional non-inverting terminal to which a CMFB signal can be input to front end CCI_LNAs.

With respect to the provision of CMFB to the front end LNAs (i.e., each signal LNA 110 and the reference LNA 112), it should be noted that in accordance with embodiments of the present disclosure, the front end LNAs are single-ended amplifiers, rather than differential amplifiers. More particularly, the front end LNAs are CCI_LNAs 120 as shown in FIG. 2A (i.e., the neural signal amplifier 100 provides single-ended signal CCI_LNAs 110 and a single-ended reference CCI_LNA 112). Unfortunately, the CMFB technique described above requires that the front end LNAs be differential amplifiers, and the CMFB signal be applied to the non-inverting inputs of the differential front end LNAs. However, in accordance with embodiments of the present disclosure, the front end LNAs are single-ended LNAs, i.e., CCI_LNAs 120, which lack a conventional non-inverting terminal to which a CMFB signal can be input, as indicated in FIG. 2C. In other words, the CCI_LNAs 120 do not have an obvious or conventionally defined non-inverting terminal to which the CMFB signal can be input.

The inventors of the present application recognized that the power supply rejection (PSR) of a CMOS inverter amplifier is typically close to unity, and has a non-inverting phase shift. The inventors of the present application thus theorized and subsequently verified that the supply terminal (e.g., which can be defined as a positive supply terminal) and/or the ground terminal of each front end CI_OTA 200 can be used as a set of non-inverting input terminals to which the CMFB signal can be applied. In other words, the supply and/or ground terminals of each front end CI_OTA 200 can be coupled to receive the CMFB signal produced by the CMFB signal generator 500 to establish an SR-CMFB configuration for the neural signal amplifier 100.

Thus, in a neural signal amplifier 100 configured for SR-CMFB in accordance with an embodiment of the present disclosure, the CMFB generator 500 includes for any given channel a signal input coupled (e.g., capacitively coupled) to the output of each front end signal CCI_LNA 110 for that channel; and a reference input coupled (e.g., capacitively coupled) to the output of the front end reference CCI_LNA 112. The CMFB signal generator 500 further includes at least one output coupled to the supply terminal or the ground terminal of the CI_OTA 200 of each front end signal CCI_LNA 110 as well as the CI_OTA 200 of the front end reference CCI_LNA 112. In various embodiments, the CMFB signal generator 500 includes a first or supply output coupled to the supply terminal of the front end CI_OTA 200 of each signal CCI_LNA 110 and the reference CCI_LNA 112; and a second or ground output coupled to the ground terminal of the front end CI_OTA 200 of each signal CCI_LNA 110 and the reference CCI_LNA 112, as further elaborated upon hereafter.

Figures 3D, 3E:
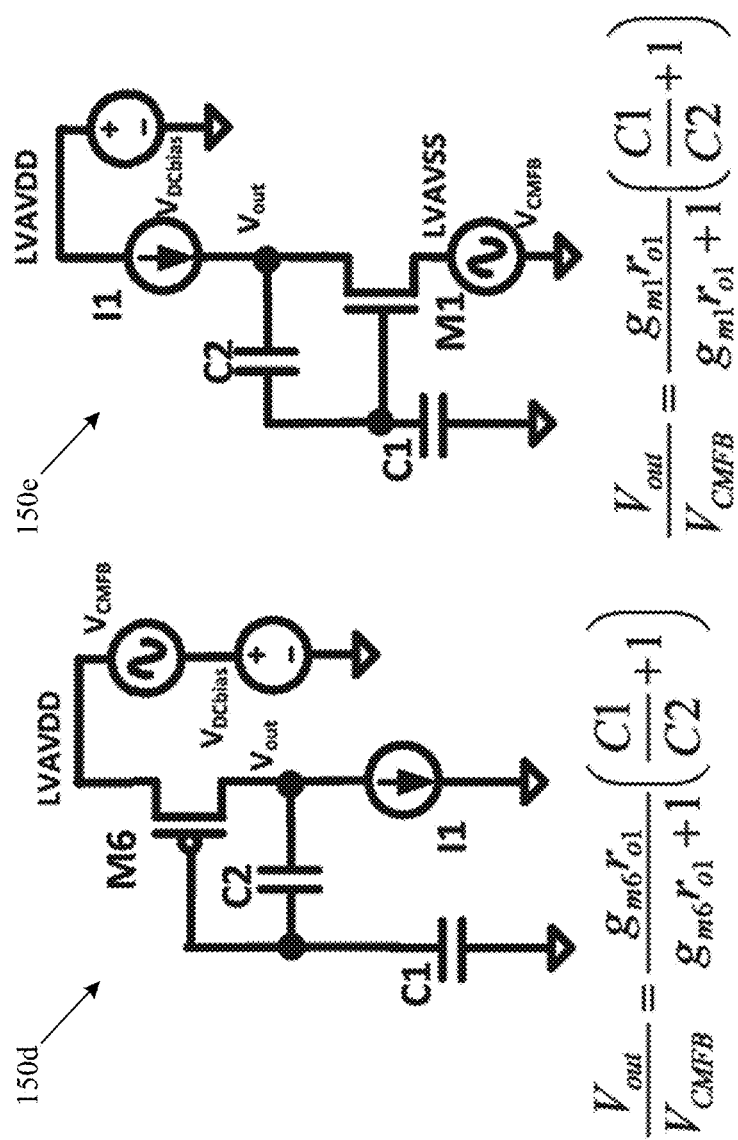

FIGS. 3A-3C show three possible circuit configurations 150a-c for establishing a non-inverting input terminal for a front end CI_OTA 200 by way of the CI_OTA's supply terminal (LNAVDD) and/or ground terminal (LNAVSS). FIGS. 3A-3C additionally show a transfer function corresponding to each such circuit configuration 150a-c. It should be noted that the circuit configurations 150a-c of FIGS. 3A-3C are not the only possible configurations for establishing a non-inverting input terminal for a CI_OTA 200 by way of its LNAVDD and LNAVSS terminals; other possible circuit configurations 150d-e and their transfer functions are shown in FIGS. 3D-3E. As indicated in FIGS. 3A-3E, the transfer functions indicate these circuit configurations 150a-e can achieve a non-inverting signal gain.

With respect to FIGS. 3A-3C, for input variations on LNAVDD with a fixed voltage on LNAVSS, i.e., the circuit configuration 150a of FIG. 3A, a corresponding variation on the biasing current and the input referred noise was observed, leading to input CMI modulated power consumption and noise injection. Therefore, if the CMFB signal is fed back solely through LNAVSS, the power consumption and input referred noise level of the CI_OTA 200 would be modulated by any CMI. The same issue also arises when LNAVSS is modulated while the voltage on LNAVDD is held constant, i.e., in the circuit configuration 150b of FIG. 3B. Hence, while the circuit configurations 150a-b of FIGS. 3A-3B can be used to establish a non-inverting input terminal for a front end CI_OTA 200, a need exists for another circuit configuration 150c for which such issues do not arise.

In various embodiments, a better or best circuit configuration 150c by which a non-inverting input terminal for the CI_OTA 200 can be provided is shown in FIG. 3C. In this circuit configuration 150c, LNAVDD and LNAVSS are driven by the CMFB signals (e.g., a first or LNAVDD CMFB signal and a second or LNAVSS CMFB signal output by the CMFB signal generator 500) concurrently, while a fixed DC voltage is maintained across both supply and ground rails. Therefore, a biasing current that is independent of the CMI signal flows through the CI_OTA 200, and hence does not lead to any CMI modulated input referred thermal noise or power consumption. Additionally, the non-inverting gain for the circuit configuration 150c of FIG. 3C is higher than that for the circuit configurations 150a,b of FIGS. 3A and 3B. Hence, various embodiments in accordance with the present disclosure utilize the circuit configuration 150c of FIG. 3C for establishing CMFB through the supply terminals or rails of the CI_OTA 200 of each front end CCI_LNA 120.

Figure 4A:
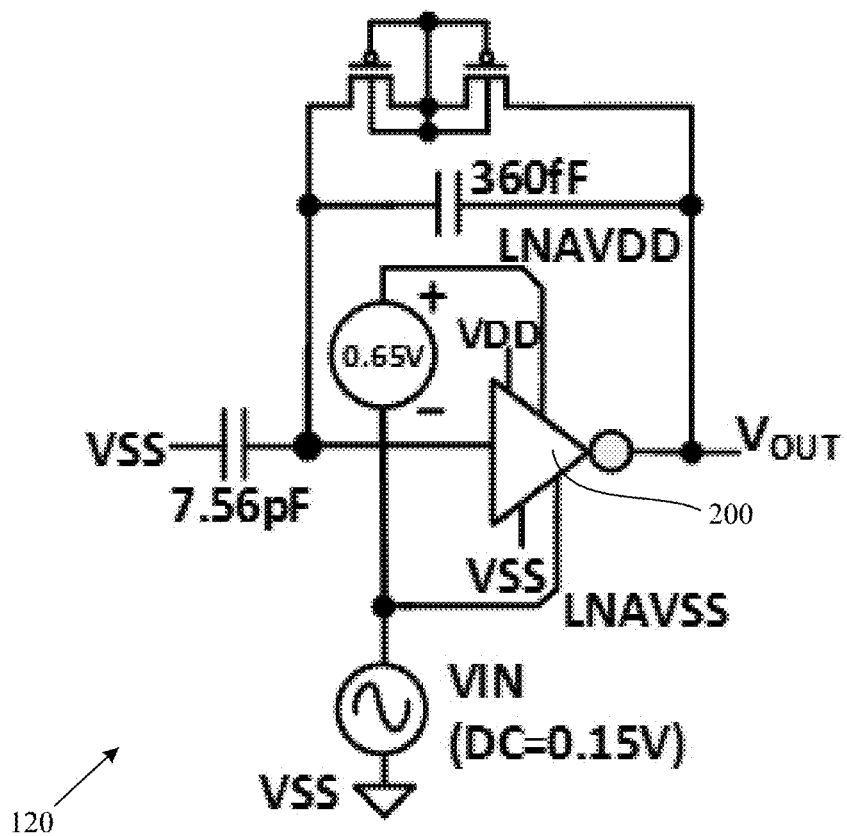
FIG. 4A shows a simulation set up for validating a non-inverting gain function by way of concurrently modulating the supply and ground rails of the CI_OTA in accordance with an embodiment of the present disclosure.
Figure 4B:
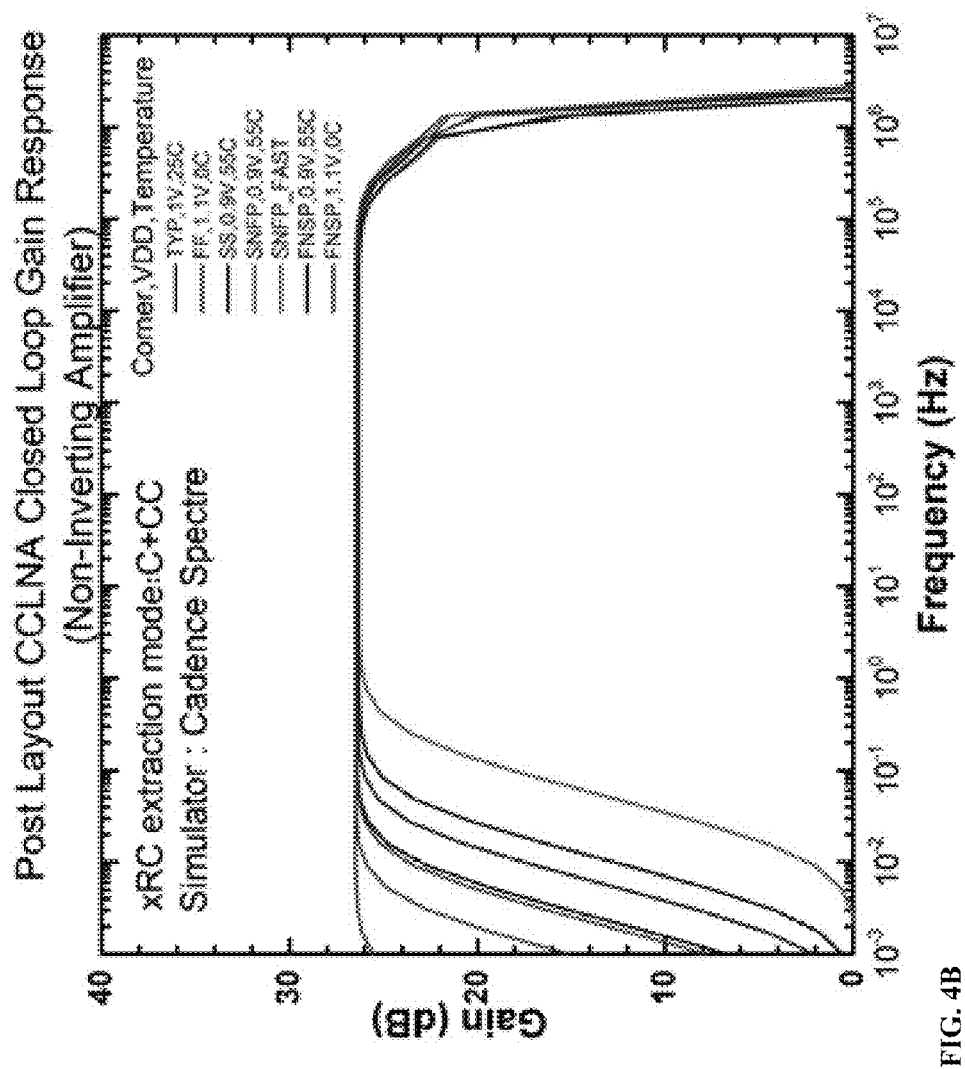
FIG. 4B and FIG. 4C show a simulated AC gain response and a simulated AC phase response, respectively, corresponding to FIG. 4A.
Figure 4C:
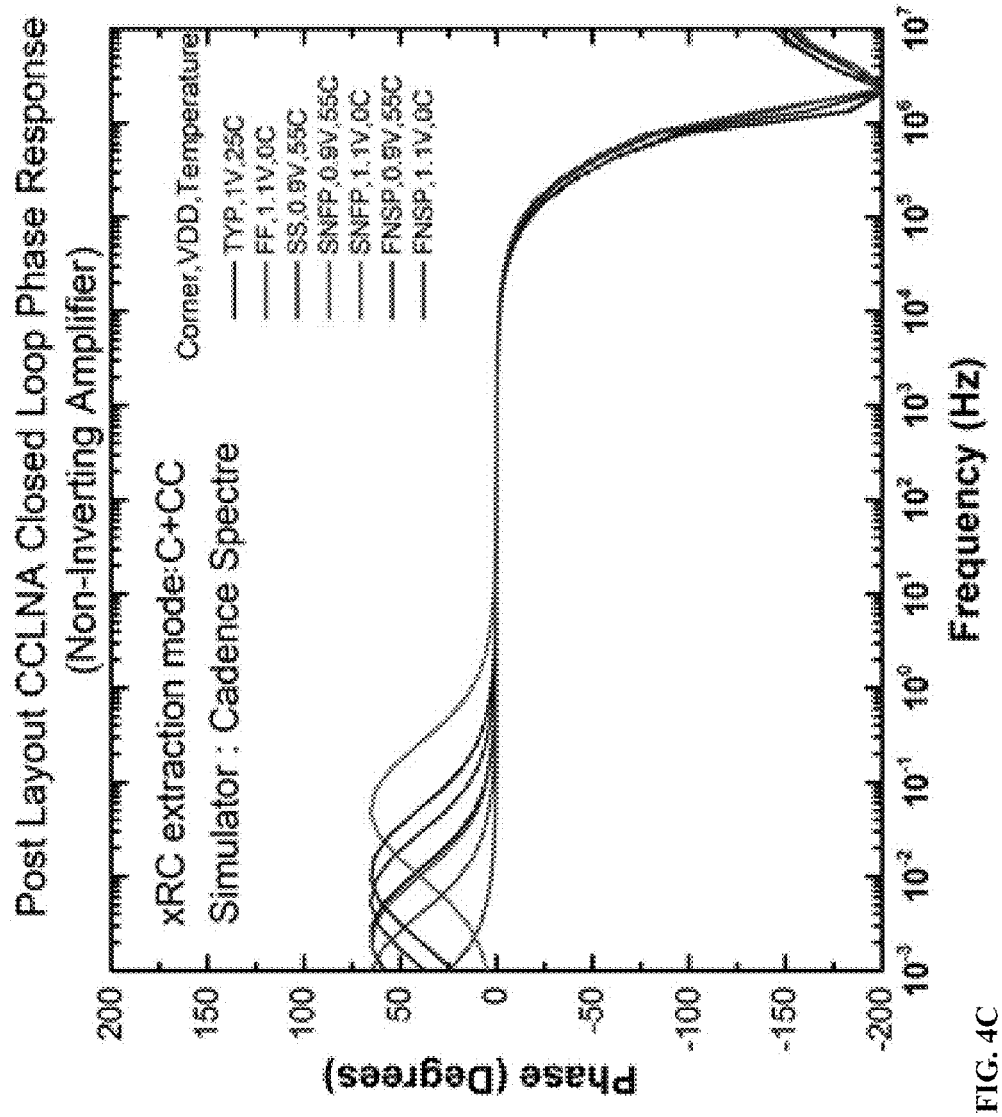

FIG. 4A shows a simulation set up for validating the non-inverting gain function by way of concurrently modulating the supply and ground terminals or rails of the CI_OTA 200. FIG. 4B shows a corresponding simulated AC gain response, and FIG. 4C shows a corresponding simulated AC phase response. The gain response indicates that an accurate mid-band closed loop gain is obtained, and the phase response indicates that the closed loop transfer function is non-inverting.

In view of the foregoing and with reference again to FIG. 2A, a CMFB loop for a neural signal amplifier 100 having a front end that utilizes single ended CCI_LNAs 120 with CI_OTAs 200 therein can be established by generating a set of CMFB signals with the CMFB signal generator 500, and concurrently feeding this set of CMFB signals through the LNAVDD and/or LNAVSS terminals or rails of each front end CI_OTA 200. Such a CMFB technique can be referred to as "CMFB through the supply rails," or SR-CMFB. In various embodiments, the CMFB signal generator 500 includes a first output configured to provide the first or LNAVDD CMFB signal to the supply terminal of the front end CI_OTA 200 of each signal CCI_LNA 110 and the reference CCI_LNA 112; and a second output configured to provide the second or LNAVSS CMFB signal to the ground terminal of the front end CI_OTA 200 of each signal CCI_LNA 110 and the reference CCI_LNA 112.

Figure 5A:
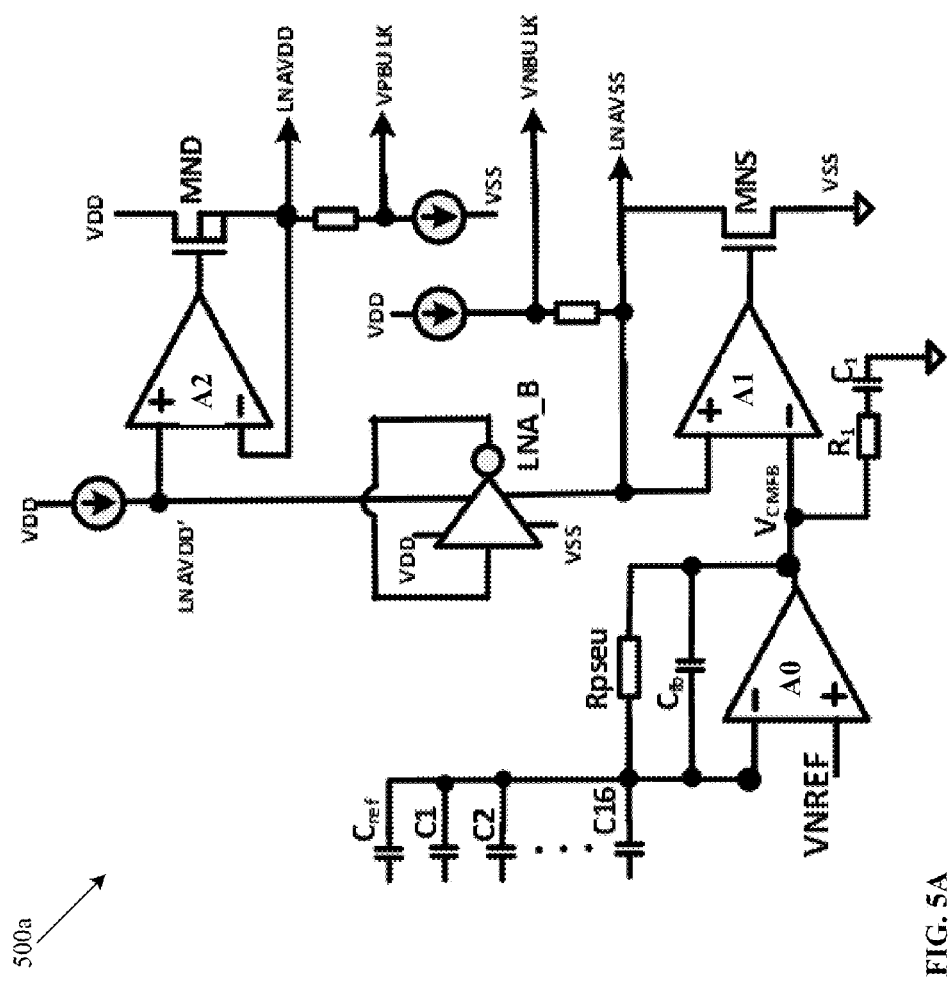
FIGS. 5A and 5B illustrate circuit diagrams for two representative CMFB signal generators in accordance with embodiments of the present disclosure.
Figure 5B:
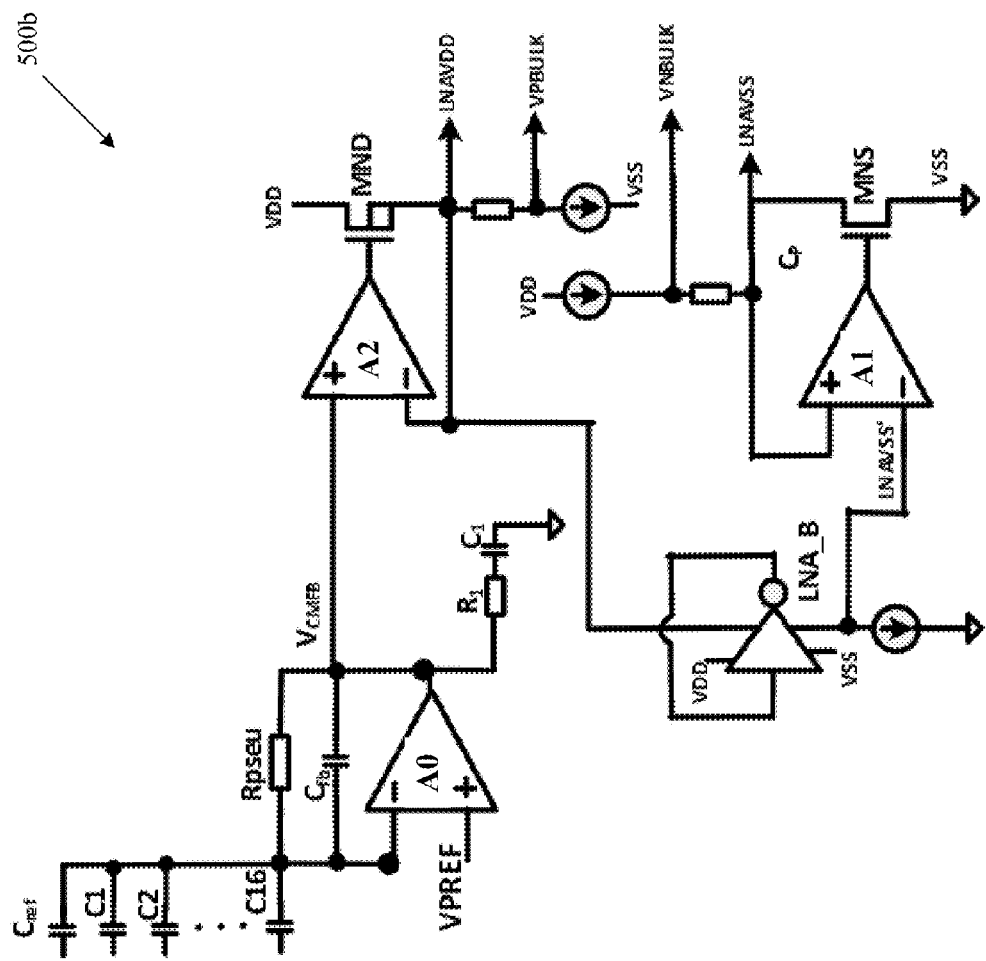
Figure 5C:
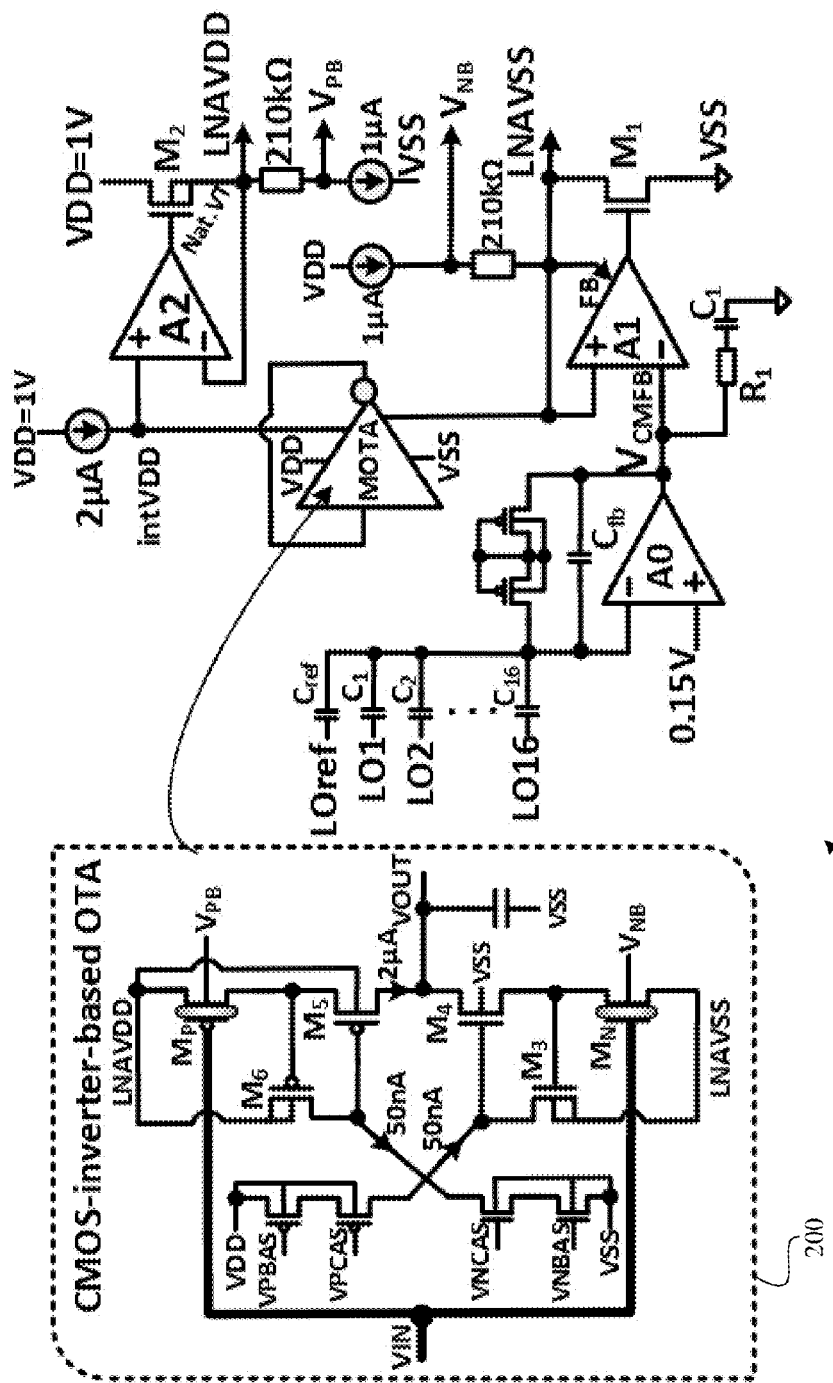
FIG. 5C is a representative CMFB signal generator corresponding to the CMFB generator of FIG. 5A, which has a CI_OTA therein.

FIGS. 5A and 5B illustrate circuit diagrams for two representative CMFB generators 500a,b in accordance with embodiments of the present disclosure, and FIG. 5C is a representative CMFB generator 500c corresponding to the CMFB generator 500a of FIG. 5A, which has a CI_OTA 200 therein. With detailed consideration of FIG. 5C, the CMFB generator 500c produces the set of CMFB signals (i.e., the first and second CMFB signals) and embeds the set of CMFB signals concurrently on the LNAVDD and LNAVSS rails of the CL_OTAs 200. The outputs of each CCI_LNA 120 are averaged by a summing circuit formed by A0, $C_{1-16}$, and $C_{fb}$. The reference voltage $V_{LS}$ sets the DC level of the summing circuit's output at 0.15V. On-chip, $V_{LS}$ can be generated by passing a 1 μA current through a 150 kΩ resistor. $R_1$ and $C_1$ help stabilize the CMFB loop. The output of the summing circuit, $V_{CFMB}$, is buffered by a unity-gain driver formed by A1 and $M_1$ in series-shunt feedback configuration, which in turn drives the LNAVSS terminals of all of the CC_LNAs. Individuals having ordinary skill in the art will recognize that other configurations of realizing this unity gain buffer is possible. A corresponding voltage, intVDD, is generated by passing a fixed current of 2 μA through a master OTA (MOTA), which has an CI_OTA 200 identical to that used in each CCI_LNA 120, and this voltage is buffered by a unity-gain driver formed by A2 and $M_2$ also connected in series-shunt feedback configuration, which in turn drive the LNAVDD terminals of all of the CCI_LNAs 120. Individuals having ordinary skill in the art will recognize that other configurations of realizing this unity gain buffer is possible. $M_2$ is a native NMOS transistor configured as a common-drain amplifier. This topology is selected instead of a PMOS transistor connected in a common-source configuration because the latter approach was found to require a much larger transistor size. As the $V_{th}$ of $M_2$ is negative, the output of A2 does not need to swing higher than intVDD.

The voltage across LNAVDD and LNAVSS is effectively fixed to the voltage across the MOTA of 0.65 V regardless of the concurrent voltage variations of LNAVDD and LNAVSS. This 0.65 V voltage difference establishes the bias current of the CI_OTAs 200 in the signal and reference CCI_LNAs 120 and makes them closely match the 2 μA current flowing through the MOTA. This method of mirroring the reference 2 μA bias current to bias all the CI_OTAs is independent of any process, voltage and temperature variations. Voltages $V_{NB}$ and $V_{PB}$ provide bulk biasing to the OTA's transistors ($M_P$ and $M_N$) and closely track variations in LNAVDD and LNAVSS, respectively. The 2 μA source current is implemented using an ultra-low compliance voltage current mirror. This allows voltage intVDD to swing close to the 1 V supply rail without causing the source current to drop out. Individuals having ordinary skill in the art will recognize that this configuration is not limited to 0.65V biasing voltage.

Figure 6A:
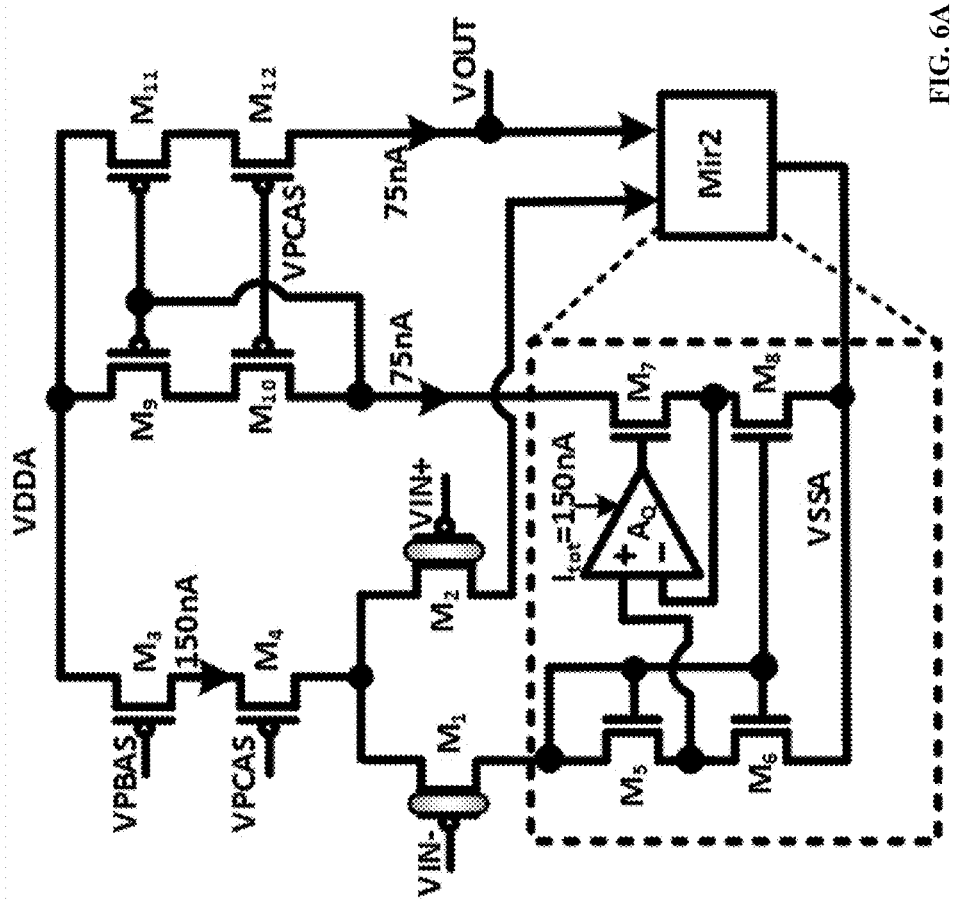
FIG. 6A shows a representative circuit schematic of OTA A0 of FIG. 5C.

FIG. 6A shows the circuit schematic of OTA A0 of FIG. 5C. In a representative implementation, A0 is a symmetrical cascode OTA having PMOS differential input pair ($M_1$ and $M_2$). Individuals having ordinary skill in the relevant art will understand that A0 can be implemented using another OTA circuit topology. With respect to this implementation, since large gate leakage currents affects the DC biasing established by the pseudo-resistor feedback resistor, both $M_1$ and $M_2$ are implemented using 2.5V thick-gate oxide transistors having negligible gate leakage currents. In the presence of large input CMI, the output of A0 would swing close to 0V (VSS), therefore both of its low side current mirrors are implemented with ultra-low compliance voltage current NMOS current mirrors (O. Charlon and W. Redman-White, "Ultra high compliance CMOS current mirrors for low voltage charge pumps and references," *Proc. European Solid-State Circuits Conference*, 2004, pp. 227-230). Using these current mirrors allows the output of A0, in the presence of a large input CMI, to drop to as low as 50 mV above VSS without severe signal distortion. The amplifier $A_Q$ that is part of the NMOS current mirror is implemented using a two stage Miller OTA having PMOS input differential pairs. The total current consumed by A0 (including that of $A_Q$) is only 600 nA. Individuals having ordinary skill in the art will recognize that other configurations for realizing $A_Q$ is possible.

Figure 6B:
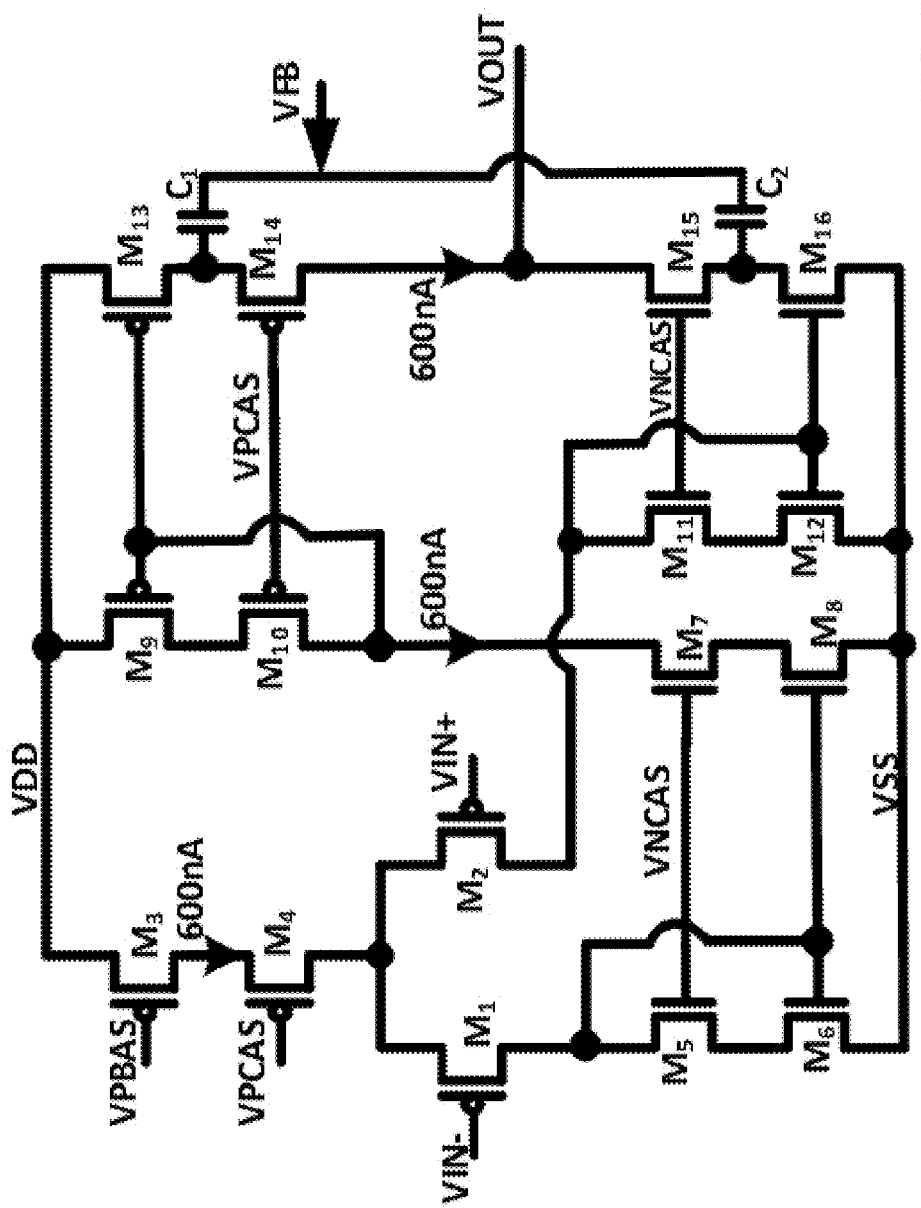
FIG. 6B shows a representative circuit schematic of OTA A1 of FIG. 5C.

FIG. 6B shows the circuit schematic of OTA A1 of FIG. 5C. In a representative implementation, A1 is a symmetrical cascode OTA having PMOs differential input pair ($M_1$ and $M_2$). Individuals having ordinary skill in the relevant art will recognize that A1 can be implemented by way of another OTA circuit topology. In this representative implementation, compared to A0, A1 is part of a series shunt feedback loop, and its output would not experience large voltage swings close to VSS. Therefore, its low side active load is implemented using conventional cascode current mirrors. Ahuja's frequency compensation technique (B. K. Ajuha, "An improved frequency compensation technique for CMOS operational amplifiers," *IEEE J. Solid-State Circuits*, vol, 18, no. 6, pp. 629-633, December 1983) is incorporated into A1 to provide power efficient frequency compensation in the local feedback loop formed by A1 and $M_1$.

Figure 6C:
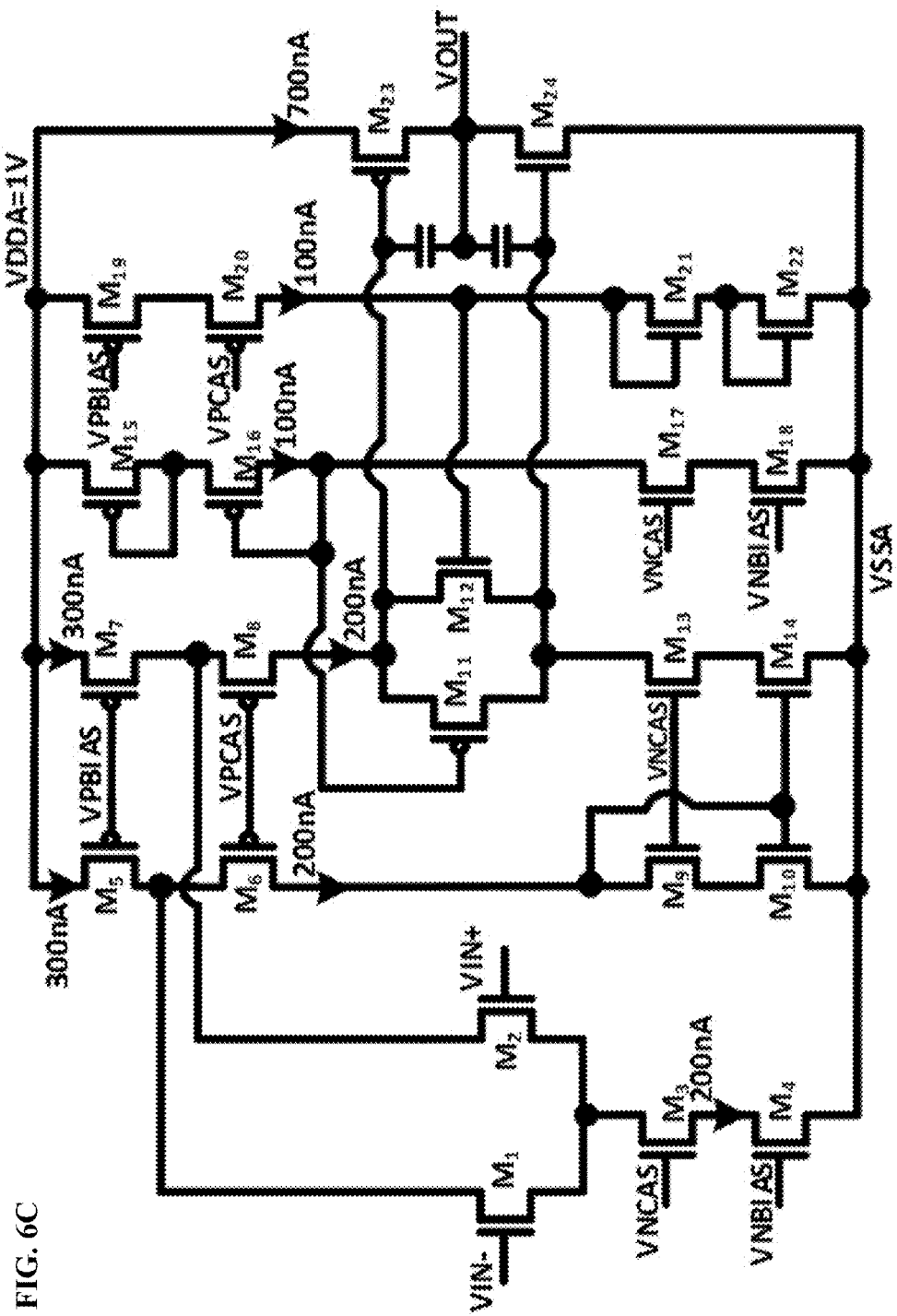
FIG. 6C shows a representative circuit schematic of Opamp A2 of FIG. 5C.

FIG. 6C illustrates a representative circuit schematic of Opamp A2 of FIG. 5C, which includes a folded cascode operational amplifier (op-amp) with an NMOS input differential pair. Consuming only 1.5 μA, A2 has a translinear class AB output stage that helps achieve good transient load response when it is connected together with $M_2$ in unity gain feedback configuration. Individuals having ordinary skill in the art will recognize that Opamp A2 is not limited to the circuit topology shown, but can be implemented by way of another opamp circuit topology.

The total quiescent current consumption of the CMFB generator circuit 500c of FIG. 5C is 9.3 μA, excluding the current supplied to the remaining CI_OTAs 200.

Aspects of Maintaining High CMRR Across the Neural Signal Amplifier's Bandwidth With reference again to FIG. 2A, in various embodiments of the neural signal amplifier 100, buffering the outputs of each signal CCI_LNA 120 and the reference CCI_LNA 120 can maintain high CMRR across the neural signal amplifier's operating frequency range.

Aspects of Buffering Signal LNA Outputs

More particularly, CMRR can be enhanced or maintained by way of coupling a unity gain buffer 300 to the output of each front end signal CCI_LNA 120 in order to reduce the output impedance of the signal CCI_LNA 120 to reduce the aforementioned phase shift effect for low frequencies. In various embodiments, the unity gain buffer 300 is an FVF 310, and can have a circuit schematic as shown in FIG. 2A, a representative implementation of which consumed only 400 nA of current. Individuals having ordinary skill in the relevant art will recognize that one or more unity gain buffers 300 can be implemented differently than as shown in FIG. 2A, for instance, as shown in any of FIGS. 7A-7E.

Figure 8A:
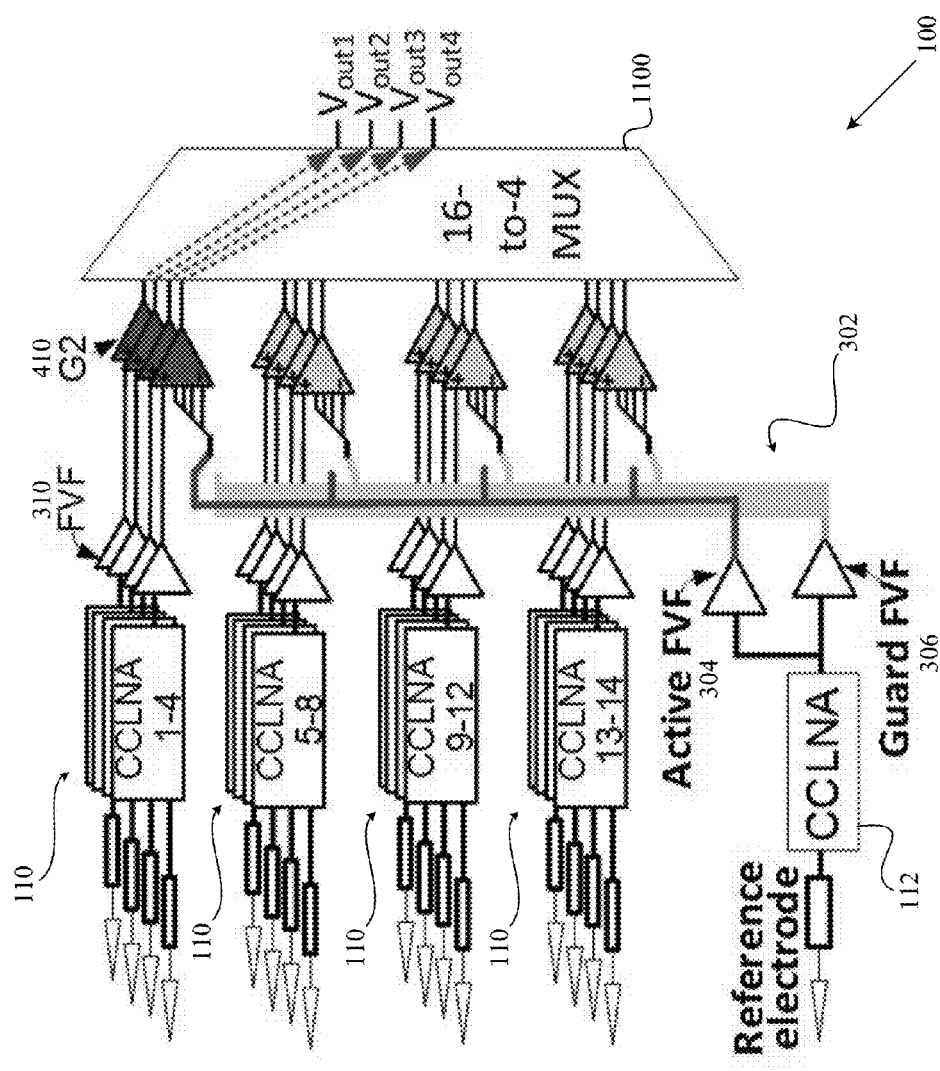
FIG. 8A illustrates a manner in which an active unity gain buffer and a guard unity gain buffer are employed in association with multiplexing distinct subsets or subgroups of second stage neural signal amplifier outputs to an output pad drive in accordance with an embodiment of the present disclosure.

Aspects of Buffering Reference LNA Outputs with Active and Guard Unity Gain Buffers As indicated in FIG. 2A and further indicated in FIG. 8A, in accordance with embodiments of the present disclosure, the outputs of the second stage amplifier 400/G2 are not all coupled to the output pad driver 1200 at any given time. Rather, at any given time, with respect to the N channels of the neural signal amplifier 100 only (d where d can be >=1) second stage amplifier outputs are actively coupled to the output pad driver 1200 and hence provided to the set of output pads by way of the set of multiplexors 1102, while the remaining second stage amplifier outputs (N−d) are not multiplexed to the set of output pads. Thus, distinct predetermined subsets or subgroups of second stage amplifier outputs are sequentially multiplexed to the set of output pads in a user determined sequential or cyclical manner across time. As a result, the capacitive load experienced by the reference LNA 112 is reduced by the factor (N/d), which significantly reduces the load capacitance mismatch between the reference LNA 112 and each signal LNA 110, and consequently reduces the aforementioned phase shift effect.

In view of the foregoing, CMRR can be further enhanced or maintained across the entire operating frequency range of the neural signal amplifier 100 by way of coupling a pair of unity gain buffers 302 to the output of the reference CCI_LNA 112, where within the pair of unity gain buffers 302, at any given time one unity buffer 304 can be defined as an active (A) unity gain buffer 304, while the other unity gain buffer 306 can be defined as a guard (G) unity gain buffer 306. During any particular multiplexing time interval, the active unity gain buffer 304 corresponding to that time interval drives (d) second stage amplifier reference inputs. Individuals having ordinary skill in the relevant art will recognize that the reference input of each of the remaining (N−d) reference inputs of the second stage amplifiers 410/G2 that are not being actively multiplexed to the set of output pads still need to track the output of the output of the reference CCI_LNA 112 during the multiplexing time interval under consideration in order to eliminate dead time when a subset or subgroup of (of size d) second stage amplifier outputs that was previously dormant becomes the active subset or subgroup of second stage amplifier outputs that are driven to the set of output pads. Thus, in various embodiments, in association with the time-multiplexing of a first active subset or subgroup of second stage amplifiers 410/G2 having their outputs driven to the set of output pads, another (e.g., adjacent) second subset or subgroup of (d) of second stage amplifiers is switched over from being driven by the guard unity gain buffer 306 to be driven by the active unity gain buffer 304, while the previously active first subset or subgroup of second stage amplifiers 410/G2 is switched over to be driven by the guard unity gain buffer 306.

Figure 8B:
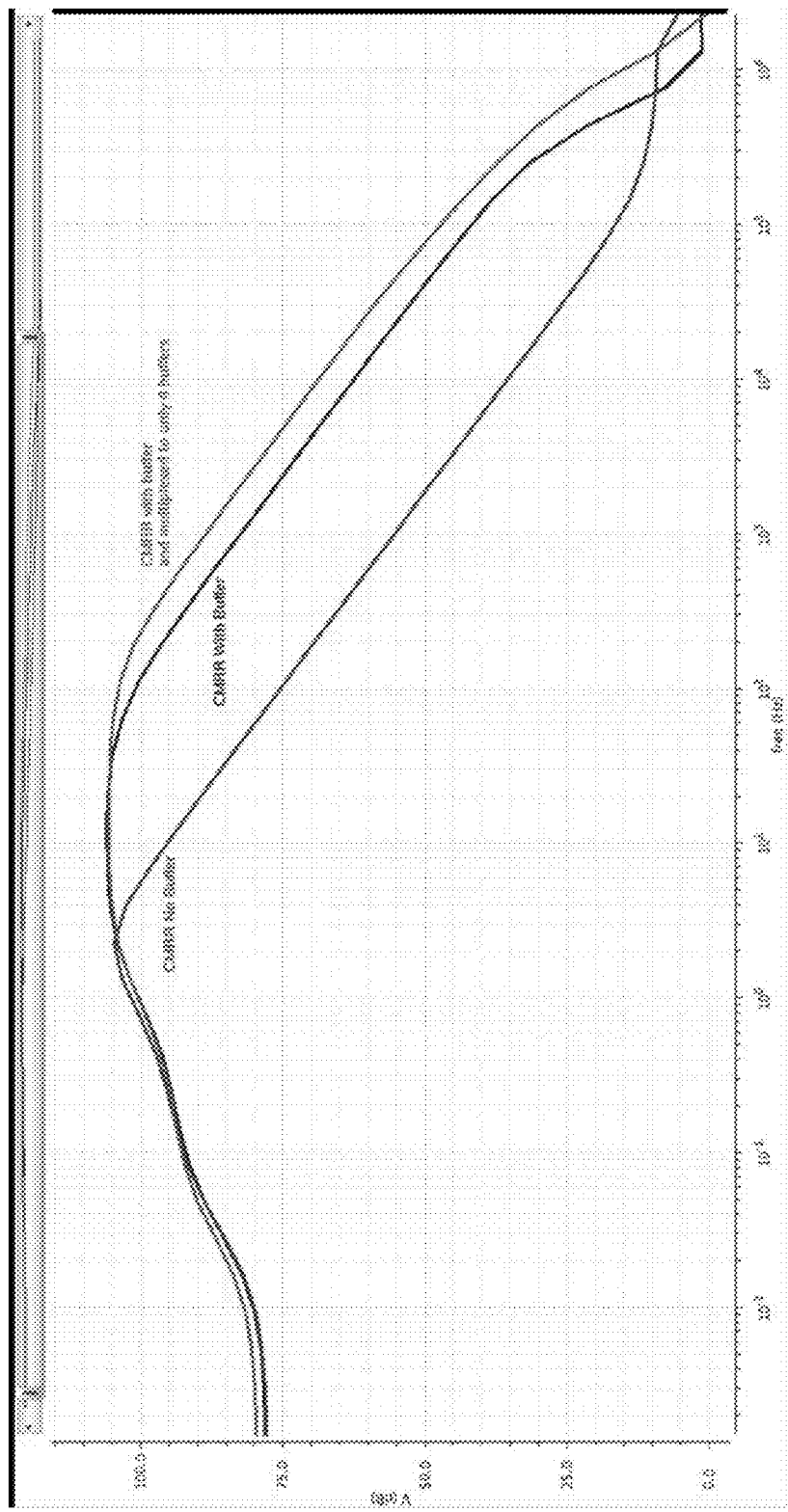
FIG. 8B shows ICMRR simulation results when a unity gain buffer is coupled to the outputs of each signal LNA, and an active unity gain buffer and a guard unity gain buffer are each coupled to the output of a reference LNA in accordance with an embodiment of the present disclosure.

FIG. 8B shows ICMRR simulation results corresponding to coupling unity gain buffers 300 to the outputs of the signal LNAs 110, and coupling the output of the reference LNA 112 to a pair of unity gain buffers 302 having an active unity gain buffer 304 and a guard unity gain buffer 306 in the manner described above. In this specific embodiment, d=4. It can be seen that in a neural signal amplifier 100 in accordance with an embodiment of the present disclosure, the use of unity gain buffers 300 at the outputs of the signal LNA 110 significantly or greatly enhances ICMRR compared to a conventional neural signal amplifier 1, and the use of the active unity gain buffer 304 and the guard unity gain buffer 306 at the output of the reference LNA 112 further enhances ICMRR.

In view of the disclosure herein, individuals having ordinary skill in the relevant art will understand that certain neural signal amplifier embodiments in accordance with the present disclosure can buffer the outputs of each signal CCI_LNA 110 by way of a unity gain buffer 300, and/or buffer the output of the reference CCI_LNA 112 by way of an active/guard buffer pair 302 as set forth above, without providing or enabling the provision of SR-CMFB or CMFB to the input stage 102. Thus, in specific embodiments, a neural signal amplifier can: (a) utilize (i) buffers such as unity gain buffers 300 coupled between the output of each front end signal LN 110 and the signal input of its corresponding second stage amplifier 410/G2, and/or (ii) an active/guard buffer pair 302 coupled to the output of the front end reference LNA 112 where at any given time, an active buffer 304 of the pair 302 is coupled to a subset or subgroup of second stage amplifier inputs corresponding to second stage amplifier outputs being actively multiplexed to multiplexor outputs, while a guard buffer 306 of the pair 302 is coupled to other second stage amplifier inputs corresponding to second stage amplifier outputs not being actively multiplexed to multiplexor outputs; and (b) omit, exclude, or avoid the use or provision of SR-CMFB or CMFB to the input stage 102, for instance, by way of omitting the CMFB signal generator 500 or decoupling it from the LNAVDD terminal and/or LNAVSS terminal of each signal LNA 110 and the reference LNA 112.

Aspects of a Fabricated Neural Signal Amplifier

Figure 9:
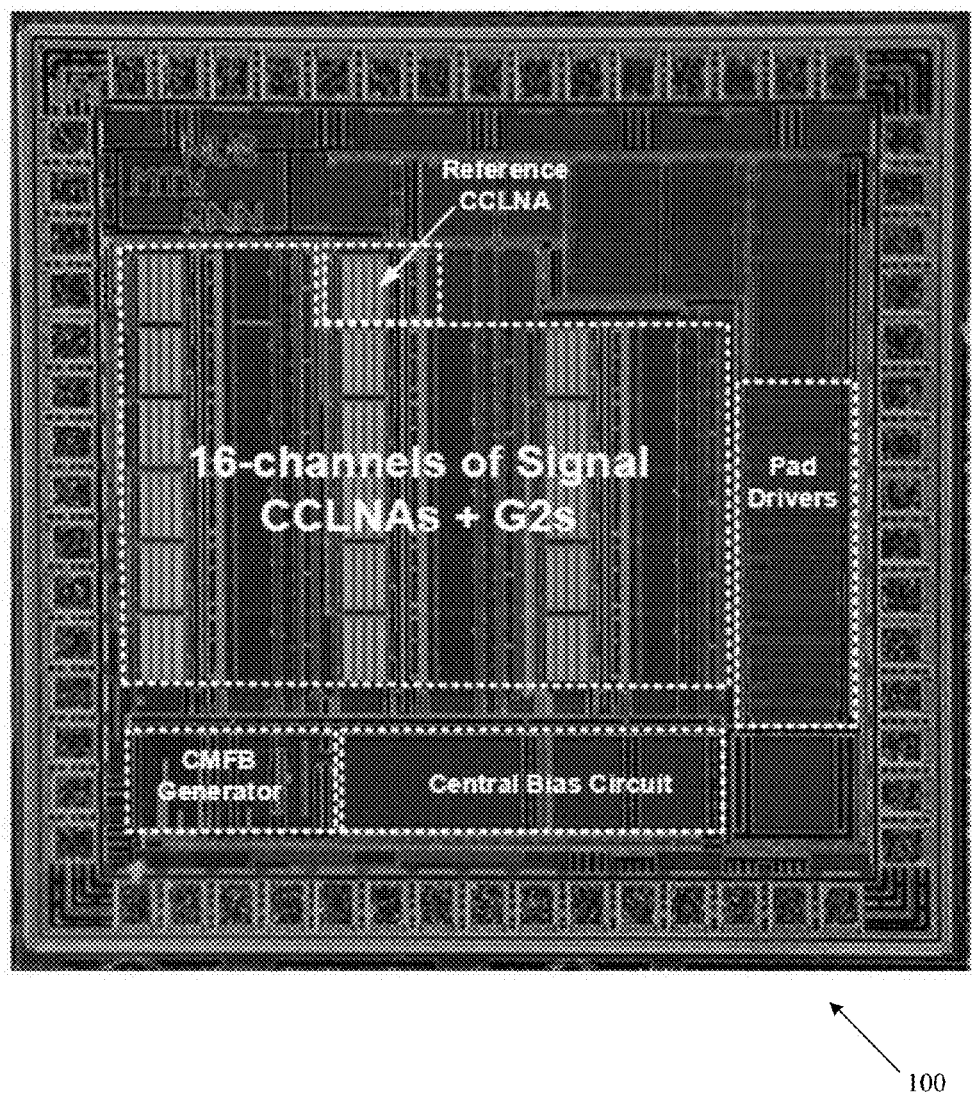
FIG. 9 is a chip micrograph showing a representative as-fabricated neural signal amplifier in accordance with an embodiment of the present disclosure.

FIG. 9 is a chip micrograph showing a representative as-fabricated neural signal amplifier 100 in accordance with an embodiment of the present disclosure. Table 1 below indicates the current consumption of particular circuit blocks of this as-fabricated neural signal amplifier 100.

TABLE 1

Current Consumption Breakdown of the Neural signal amplifier Chip

| Circuit Block | Current consumption (µA) | Percentage of Total (%) |
| --- | --- | --- |
| All | 49.6 | 41.9 |
| Signal CC_LNA + FVF + G2 | (3.1 µA/channel) | |
| Reference CC_LNA + Active/Guard FVF | 2.9 | 2.4 |
| CMFB Generator | 9.3 | 7.9 |

TABLE 1-continued

Current Consumption Breakdown of the
Neural signal amplifier Chip

| Circuit Block | Current consumption (μA) | Percentage of Total (%) |
|---|---|---|
| All Pad Drivers | 14.5 | 12.2 |
| Central bias and test circuits | 4.2 | 35.5 |
| Total | 118.3 | 100 |

The effective current consumption per amplifier channel, excluding the output driver can be calculated as $$I_{channel} = I_{signalCCLNA} + I_{signalFVF} + I_{G2} + \frac{I_{referenceCCLNA} + 2*I_{active\_guardFVF}}{16} \quad (3)$$

From Table 1, $(I_{signalCC\_LNA}+I_{signalFVF}+I_{G2})$ is 3.1 μA, and $(I_{referenceCC\_LNA}+2*I_{active\_guardFVF})$ is 2.9 μA. Hence, the effective current consumption per amplifier channel is 3.28 μA.

Figure 10A:
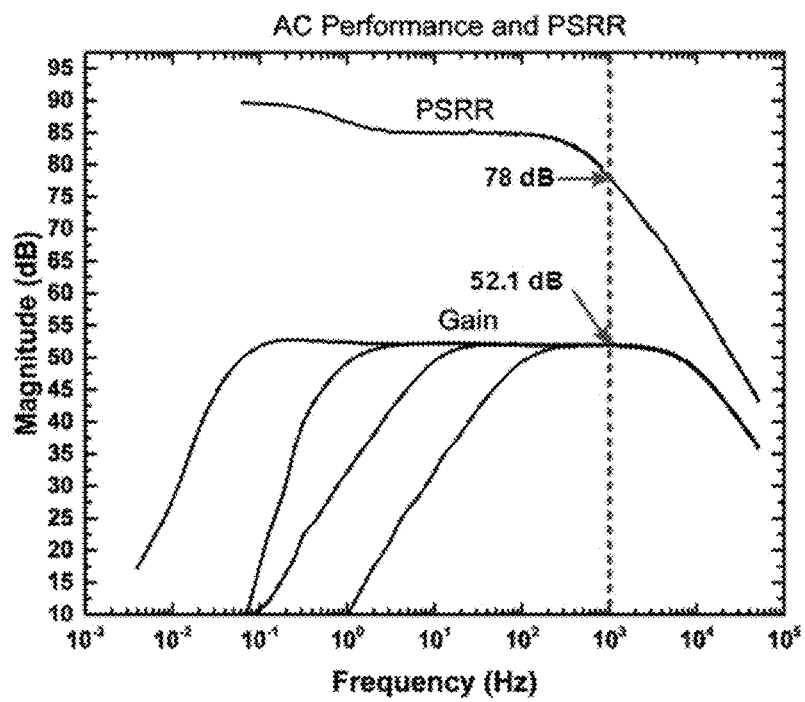
FIGS. 10A-10D illustrate measured performance characteristics of the as-fabricated neural signal amplifier of FIG. 9.
Figure 10B:
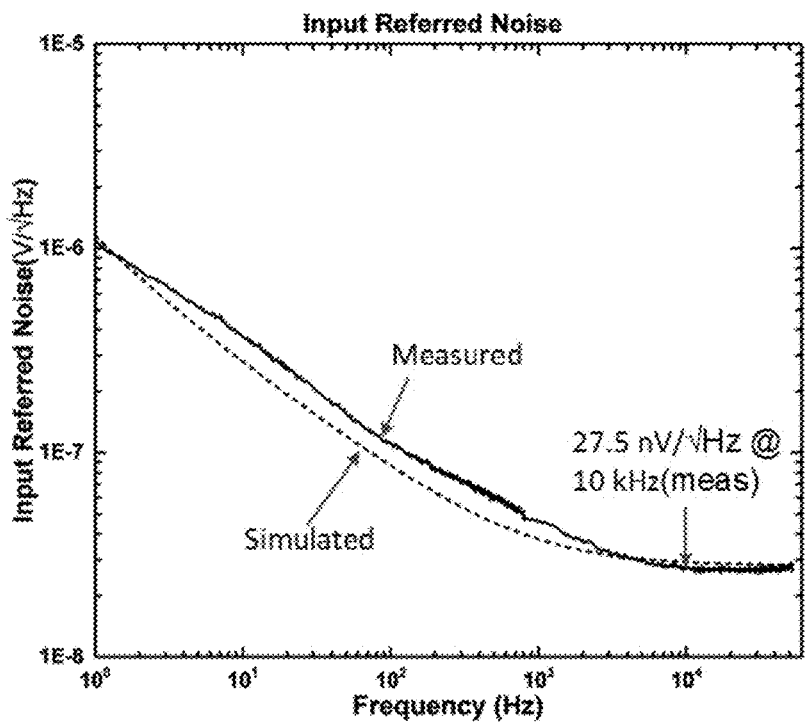

FIGS. 10A-10D illustrate certain measured performance characteristics of the as-fabricated neural signal amplifier 100 of FIG. 9. More particularly, FIG. 10A shows the AC frequency response of one channel of the overall amplifier for various values of $f_L$, which was tuned by $V_{tune}$. The amplifier has a measured low-pass cut off frequency of 8.2 kHz, and its high-pass cut off frequency is tunable from 53 mHz to 100 Hz. FIG. 10B shows the input referred noise root power spectral density (PSD). The input referred noise, when integrated over 1 Hz to 8.2 kHz signal bandwidth, is 4.13 $\mu V_{rms}$. With an effective current consumption per amplifier channel of 3.28 μA, the noise efficiency factor (NEF) and power efficiency factor (PEF) are obtained as 3.19 and 10.17, respectively.

Figure 10C:
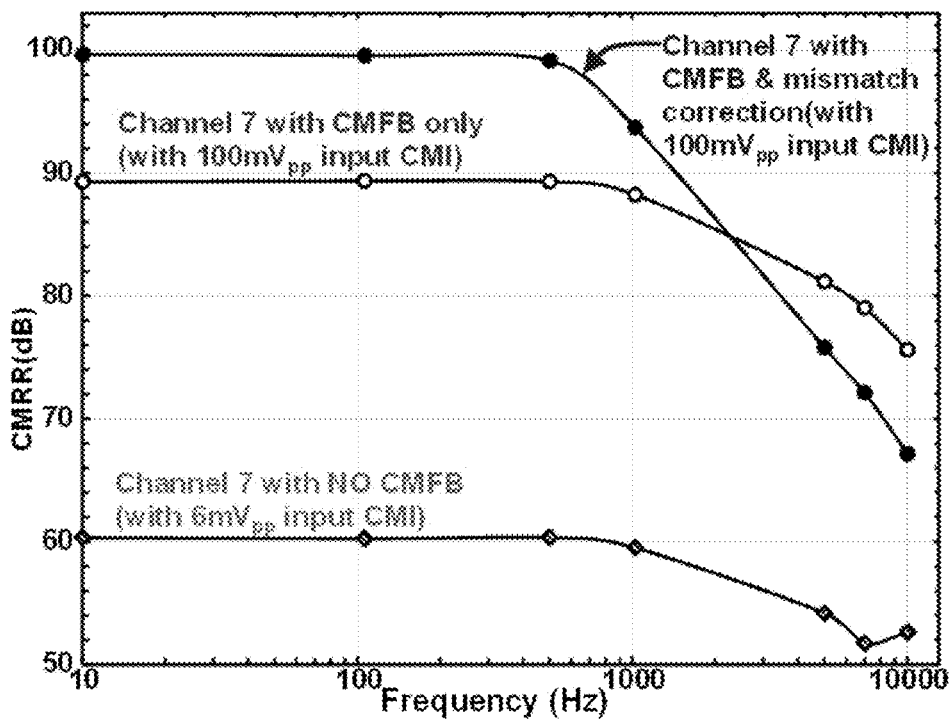

FIG. 10C shows the measured ICMRR of the as-fabricated neural signal amplifier 100 at certain point frequencies along with three different measurement setups. When the SR-CMFB loop is turned off, the ICMRR is below the minimum required value of 70 dB and cannot accommodate large input CMI amplitudes. When the CMFB through the supply rails is activated, the ICMRR increases to 90 dB and remains above 80 dB until 1 kHz. The ICMRR further increases to 99.5 dB when the mismatch correction circuit containing the 3-bit capacitor bank at the input of the second stage is activated.

Figure 10D:
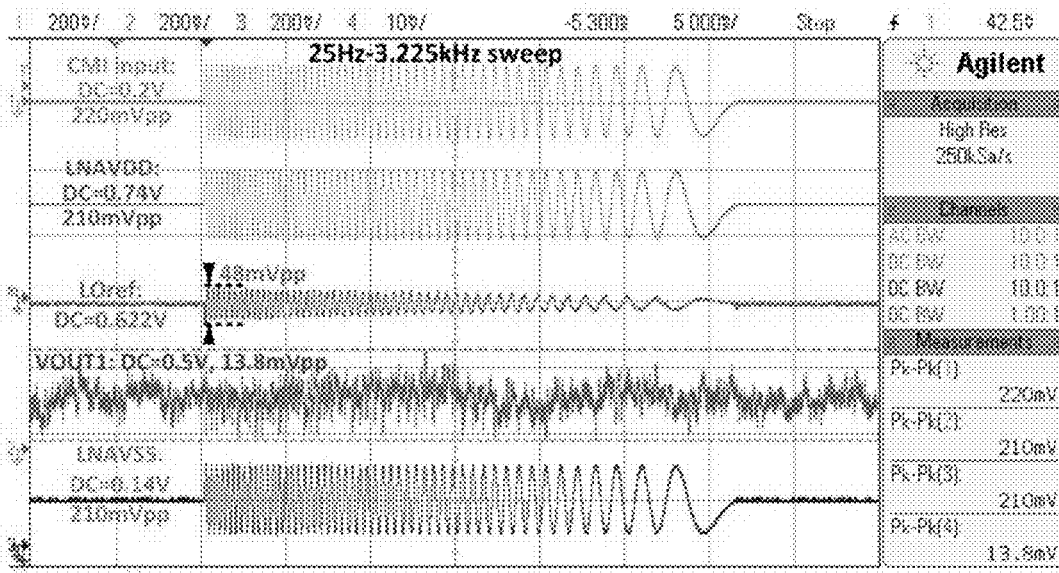

FIG. 10D illustrates this as-fabricated neural signal amplifier's ability to reject large CMI up to the limit of 200 $mV_{pp}$. The top-most waveform is the applied CMI signal composed of frequency components from 25 Hz to 3.225 kHz. The on-chip CMFB generator 500 forces LNAVDD ($2^{nd}$ waveform from top) and LNAVSS (bottommost waveform) rails of the CCI_LNAs 110 to closely track this large CMI signal. The $4^{th}$ waveform from the top shows the attenuated CMI signal at the output of the reference CCI_LNA 110. This attenuation of CMI at the outputs of the CCI_LNA 110 is due to the action of the SR-CMFB loop. Finally, after differential amplification at the second stage amplifier 410/G2, there is no obvious trace of the interfering signal at the output. FIG. 10D also shows that this technique is effective in rejecting CMIs, especially at low frequencies.

FIGS. 11A-11C show results of an experiment in which the as-fabricated neural signal amplifier 100 of FIG. 9 was used to acquire cortical signals from the dorsal medial region of an awake *Macaca fascicularis*. The experiment was conducted in accordance with protocols approved by the Institutional Animal Care and Use Committee (IACUC) of the National University of Singapore. All in vivo experiments were performed in an unshielded environment. Microarray electrodes (FIG. 11A) had been previously implanted in the cortical region of the macaque for more than 6 months prior to the neural signal recording experiment. As shown in FIG. 11B, which shows acquired neural signals from one channel, there was no observable interference from the AC mains. A time-aligned analysis of the waveform of FIG. 11B is shown in FIG. 11C, and indicates the acquired spiking activities of two active neurons in this experiment.

Aspects of particular embodiments of the present disclosure address at least one aspect, problem, limitation, and/or disadvantage associated with existing biosignal/neurosignal amplifiers. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure and the corresponding claims.

The invention claimed is:

1. A biopotential amplifier configured for detecting, sensing, recording, or amplifying biopotentials across multiple biopotential amplifier channels, the biopotential amplifier comprising:
   an input stage having a plurality of inputs and a plurality of outputs, the input stage comprising:
   a plurality of signal low noise amplifiers (LNAs) comprising a signal LNA corresponding to each channel of the multiple biopotential amplifier channels, each signal LNA for a given channel of the multiple biopotential amplifier channels having an input configured for receiving a biopotential signal corresponding to the given channel, an output, a supply terminal (LNAVDD terminal) corresponding to a positive supply rail at which a supply signal is providable, and a ground terminal (LNAVSS terminal) corresponding to a negative supply rail couplable to electrical ground; and
   a reference low noise amplifier (LNA) having an input configured for receiving a reference signal, an output, a supply terminal (LNAVDD terminal) corresponding to a positive supply rail at which a supply signal is providable, and a ground terminal (LNAVSS terminal) corresponding to a negative supply rail couplable to electrical ground;
   a second stage comprising a second stage amplification and/or processing unit, which for a given channel has each of a signal input coupled to the output of the signal LNA and an output corresponding to the given channel, the second stage amplification and/or processing unit further including at least one reference input coupled to the output of reference LNA; and a common mode feedback (CMFB) signal generator configured to provide a set of CMFB signals to at least one supply rail of the input stage.

2. The biopotential amplifier of claim 1, wherein the CMFB generator comprises:

for any given channel a signal input coupled to the output of the signal LNA for the given channel;

a reference input coupled to the output of the reference LNA; and at least one of (a) a first output coupled to the LNAVDD terminal of the reference LNA and the LNAVDD terminal of each signal LNA, and (b) a second output coupled to the LNAVSS terminal of the reference LNA and the LNAVSS terminal of each signal LNA.

3. The biopotential amplifier of claim 2, wherein the CMFB signal generator includes each of:

(a) a first output coupled to the LNAVDD terminal of each signal LNA and the LNAVDD terminal of the reference LNA, by which a first CMFB signal produced by the CMFB signal generator is providable to each signal LNA and the reference LNA; and (b) a second output coupled to the LNAVSS terminal of each signal LNA and the LNAVSS terminal of the reference LNA, by which a second CMFB signal produced by the CMFB signal generator is providable to each signal LNA and the reference LNA.

4. The biopotential amplifier of claim 1, wherein the reference LNA and each signal LNA is a single-ended amplifier.

5. The biopotential amplifier of claim 4, wherein the reference LNA and each signal LNA comprises a capacitively coupled inverter-based LNA (CCI_LNA).

6. The biopotential amplifier of claim 5, wherein the CCI_LNA comprises a CMOS inverter-based operational transconductance amplifier (CI_OTA), and wherein the CI_OTA provides the LNAVDD terminal and the LNAVSS terminal of the CCI_LNA.

7. The biopotential amplifier of claim 1, further comprising a plurality of buffers, including for each channel a first buffer coupled between the output of the signal LNA and the signal input of the second stage amplification and/or processing unit corresponding to that channel.

8. The biopotential amplifier of claim 7, wherein each buffer within the plurality of buffers comprises a unity gain buffer or a non-unity gain buffer.

9. The biopotential amplifier of claim 8, wherein each buffer within the plurality of buffers comprises a flipped voltage follower (FVF).

10. The biopotential amplifier of claim 7, further comprising:

a plurality of multiplexors having a plurality of inputs coupled to the outputs of the second stage amplification and/or processing unit and a set of multiplexor outputs, the plurality of multiplexors configured to sequentially multiplex distinct subsets of second stage amplification and/or processing unit outputs to the set of multiplexor outputs across a plurality of distinct multiplexing time intervals; and a pair of active/guard buffers within which during any given multiplexing time interval one buffer of the active/guard buffer pair operates as an active buffer and the other buffer of the active/guard buffer pair operates as a guard buffer, each of the active buffer and the guard buffer having an input coupled to the output of the reference LNA and an output, wherein during any given multiplexing time interval the output of the active buffer is coupled to a distinct subset of second stage amplification and/or processing unit outputs being multiplexed to the set of multiplexor outputs during the given multiplexing time interval, while the output of the guard buffer is coupled to other second stage amplification and/or processing unit outputs not being multiplexed to the set of multiplexor outputs during the given multiplexing time interval.

11. The biopotential amplifier of claim 10, wherein across a plurality of distinct multiplexing time intervals, each buffer of the pair of active/guard buffers alternatingly operates as the active buffer or the guard buffer from one multiplexing time interval to another multiplexing time interval.

12. The biopotential amplifier of claim 10, wherein each of the active buffer and the guard buffer comprises a unity gain buffer or a non-unity gain buffer.

13. The biopotential amplifier of claim 12, wherein each of the active buffer and the guard buffer comprises an FVF.

14. The bipotential amplifier of claim 10, wherein the plurality of multiplexor outputs is coupled to an output pad driver and/or other downstream circuitry that is coupled to a set of output pads, and wherein during any given multiplexing time interval the distinct subset of second stage amplification and/or processing unit outputs corresponding to the given multiplexing time interval is coupled to the set of output pads.

15. A method for detecting, sensing, or recording, or amplifying biopotentials across multiple biopotential amplifier channels using a biopotential amplifier having (a) an input stage comprising a plurality of inputs and a plurality of outputs, the input stage comprising a reference low noise amplifier (LNA) and a plurality of signal LNAs, the plurality of signal LNAs comprising a signal LNA corresponding to each channel of the multiple biopotential amplifier channels (b) a second stage comprising a plurality of signal inputs, at least one reference input, and a plurality of outputs, and (c) a common mode feedback (CMFB) signal generator comprising a plurality of inputs coupled to the plurality of input stage outputs and a set of outputs, the method comprising:

receiving a biopotential signal corresponding to each channel of the multiple biopotential amplifier channels at an input of a signal LNA corresponding to the channel, each signal LNA for a given channel of the multiple biopotential amplifier channels including an input, an output, a supply terminal (LNAVDD terminal), and a ground terminal (LNAVSS terminal);

receiving a reference signal at a reference input of the reference LNA of the input stage, the reference LNA including an input, an output, a supply terminal (LNAVDD terminal), and a ground terminal (LNAVSS terminal);

coupling signals output by the signal LNAs to corresponding signal inputs of a second stage amplification and/or processing unit of the second stage;

coupling a reference signal output by the reference LNA to at least one reference input of the second stage signal amplification and/or processing unit;

coupling signals output by each signal LNA and the reference signal output by the reference LNA to the inputs of the CMFB signal generator;

generating a set of CMFB signals with the CMFB generator corresponding to the signals provided to the CMFB signal generator inputs; and providing supply rail based CMFB (SR-CMFB) to the input stage by feeding back the set of CMFB signals to at least one of the LNAVDD terminal and the LNAVSS terminal of each signal LNA and the reference LNA.

16. The method of claim 15, wherein each signal LNA and the reference LNA is a single-ended capacitively coupled LNA (CCLNA) having an operational transconductaance amplifier (OTA) therein, and wherein the OTA corresponding to each signal LNA and the reference LNA provides the LNAVDD terminal and the LNAVSS terminal thereof.

17. The method of claim 16, wherein the OTA comprises an inverter.

18. The method of claim 15, wherein the set of CMFB signals includes a first CMFB signal and a second CMFB signal, and wherein providing SR-CMFB to the input stage comprises feeding back the first CMFB signal to the LNAVDD terminal of each signal LNA and the LNAVDD terminal of the reference LNA, and feeding back the second CMFB signal to the LNAVSS terminal of each signal LNA and the LNAVSS terminal of the reference LNA.

19. The method of claim 15, further comprising receiving the output of each signal LNA at a buffer corresponding to the signal LNA, and coupling an output of this buffer to a corresponding signal input of the second stage signal amplification and/or processing unit.

20. The method of claim 19, wherein the biopotential amplifier further comprises (d) an output stage including a plurality of multiplexors having a plurality of inputs coupled to the second stage amplification and/or processing unit outputs and a set of outputs, the plurality of multiplexors configured to sequentially multiplex distinct subsets of second stage signal amplification and/or processing unit outputs to the set of multiplexor outputs across a plurality of distinct multiplexing time intervals, and (e) an active/guard buffer pair comprising a first buffer and a second buffer, each of the first buffer and the second buffer of the active/guard buffer pair having an input coupled to the output of the reference LNA and each of the first buffer and the second buffer of the active/guard buffer pair having an output, wherein the method further comprises:

receiving the output of the reference LNA at the inputs of the first and second buffers of the active/guard buffer pair; and across a plurality of distinct multiplexing time intervals, alternatingly operating each of the first buffer and the second buffer of the active/guard buffer pair as an active buffer or the guard buffer from one multiplexing time interval to another multiplexing time interval, such that during a given multiplexing time interval, the output of the active buffer is coupled to a distinct subset of second stage amplification and/or processing unit outputs being multiplexed to the set of multiplexor outputs during the given multiplexing time interval, while the output of the guard buffer is coupled to other second stage amplification and/or processing unit outputs not being multiplexed to the set of multiplexor outputs during the given multiplexing time interval.

* * * * *